US005403823A

United States Patent [19]
Frank

[11] Patent Number: 5,403,823
[45] Date of Patent: Apr. 4, 1995

[54] ALKYL INDANE ALDEHYDE COMPOUNDS

[75] Inventor: Walter C. Frank, Holland, Pa.

[73] Assignee: Union Camp Corporation, Princeton, N.J.

[21] Appl. No.: 184,862

[22] Filed: Jan. 21, 1994

Related U.S. Application Data

[63] Continuation-in-part of Ser. No. 79,008, Jun. 18, 1993, Pat. No. 5,292,720.

[51] Int. Cl.$^6$ .............................................. A61K 7/46
[52] U.S. Cl. ...................................... 512/17; 568/440; 568/441
[58] Field of Search ................... 512/17; 568/440, 441

[56] References Cited

U.S. PATENT DOCUMENTS

| | | | |
|---|---|---|---|
| 2,800,511 | 7/1959 | Carpenter | 260/599 |
| 2,897,237 | 7/1959 | Carpenter | 260/592 |
| 3,244,751 | 4/1966 | Theimer et al. | 260/592 |
| 3,246,044 | 4/1966 | Wood et al. | 260/668 |
| 3,278,622 | 10/1966 | Stofberg et al. | 260/668 |
| 3,379,785 | 4/1968 | Kahn | 260/668 |
| 3,400,159 | 9/1968 | Theimer et al. | 260/592 |
| 3,442,640 | 5/1969 | Wood et al. | 71/124 |
| 3,509,215 | 4/1970 | Wood et al. | 260/592 |
| 3,856,875 | 12/1974 | Wood et al. | 260/668 |
| 4,018,719 | 4/1977 | De Simone | 252/522 |
| 4,162,256 | 7/1979 | Sprecker et al. | 260/345 |
| 4,284,818 | 8/1991 | Sato et al. | 568/323 |
| 4,352,748 | 10/1982 | Traas et al. | 252/522 |
| 4,406,828 | 9/1983 | Gozenbach | 252/522 |
| 4,466,908 | 8/1984 | Sprecker et al. | 252/522 |
| 4,551,573 | 11/1985 | Cobb | 585/459 |
| 4,605,778 | 8/1986 | Willis et al. | 568/433 |
| 4,652,400 | 3/1987 | Sprecker | 252/522 R |
| 4,767,882 | 8/1988 | Suzukamo et al. | 560/100 |
| 4,877,910 | 10/1989 | Frank | 585/411 |
| 4,877,911 | 10/1989 | Frank | 585/411 |
| 4,877,912 | 10/1989 | Frank | 585/411 |
| 4,877,913 | 10/1989 | Frank | 585/411 |
| 4,877,914 | 10/1989 | Frank | 585/411 |
| 4,877,915 | 10/1989 | Frank | 585/411 |
| 4,877,916 | 10/1989 | Frank | 585/411 |
| 4,880,775 | 11/1989 | Christenson et al. | 512/12 |
| 4,908,349 | 3/1990 | Gozenbach | 512/26 |
| 5,087,770 | 2/1992 | Frank | 568/327 |
| 5,087,785 | 2/1992 | Frank | 585/459 |
| 5,095,152 | 3/1992 | Frank | 568/440 |
| 5,162,588 | 11/1992 | Fehr et al. | 568/328 |
| 5,185,318 | 2/1993 | Fehr et al. | 512/16 |
| 5,206,217 | 4/1993 | Frank | 512/18 |

FOREIGN PATENT DOCUMENTS

| | | |
|---|---|---|
| 0301375 | 2/1989 | European Pat. Off. . |
| 0393742 | 10/1990 | European Pat. Off. . |
| 0405427A2 | 1/1991 | European Pat. Off. . |
| 50-40761 | 4/1975 | Japan . |
| 57-40420 | 3/1982 | Japan . |
| 7802038 | 8/1978 | Netherlands ........................ 512/17 |
| 1459036 | 12/1976 | United Kingdom . |

OTHER PUBLICATIONS

Muller and D. Lamparksy, *Perfumes, Art, Science and Technology*, Elsevier Science Publishing Co., Inc., New York, N.Y., pp. 254–310 (1991).

Bedoukian, Paul Z., Perfumery and Flavoring Synthetics, 3rd Revised Ed., pp. 334–336 (Allured Publishing Corp., Illinois 1986).

Bedoukian, Paul Z., Perfumery and Flavoring Synthetics, 2nd Revised Ed., pp. 248–292 (Elsevier Publishing Co., 1967).

Beets, Structure–Activity Relationships in Human Chemoreception, pp. 161–381 (Applied Science Publishers Ltd., London) (1973).

Carey et al., Advanced Organic Chemistry, Part B: Reactions and Sythesis, pp. 383–386 (Plenum Press, N.Y. 1977).

(List continued on next page.)

Primary Examiner—James H. Reamer
Attorney, Agent, or Firm—Woodcock Washburn Kurtz Mackiewicz & Norris

[57] ABSTRACT

The present invention relates, inter alia, to novel alkyl indane aldehyde compounds having fragrant musk-like aroma.

28 Claims, No Drawings

OTHER PUBLICATIONS

Effenberger, Electrophilic Reagents, *Angewandte Chemie* (Int. Ed. in English), vol. 19, No. 3, pp. 151–230 (1980).

Fehr et al., New Aromatic Musk Odorants: Design and Synthesis, *Helvetica Chimica Acta*, vol. 72, pp. 1537–1553 (1989).

Godfrey et al., Preparation of Methoxyphenols by Baeyer-Villiger Oxidation of Methoxybenzaldehydes, *J. C. S. Perkin I*, pp. 1353–1354 (1974).

Hannan et al., Synthesis of Bromonaphthoquinones from 1,5-Dimethoxynaphthalene, *J. Org. Chem.*, vol. 44, No. 13, pp. 2153–2158 (1979).

Harrison et al., Compendium of Organic Synthetic Methods, pp. 84–85 (Wiley–Interscience, N.Y. 1971).

Hauser et al., Regiospecific Oxidation of Methyl Groups in Dimethylanisoles, *Synthesis*, pp. 723–724 (1987).

Huang et al., A Convenient Synthesis of Aryl Formatest, *J. Chem. Research* (Synop), pp. 292–293 (1991).

Imatoto et al., Cerium(IV) Trifluoromethanesulfonate as a Strong Oxidizing Agent, *Chemistry Letters*, pp. 1445–1446 (1990).

Kreh et al., Selective Oxidations With Ceric Methanesulfonate and Ceric Trifluoromethanesulfonate, *Tetrahedron Ltrs*, vol. 28, No. 10, pp. 1067–1068 (1987).

Laing et al., Synthetic Steroids. Part IX. A New Route to 19-Nor-steroids, *J. Chem. Soc.* (C), pp. 2915–2918 (1968).

March, J., Advanced Organic Chemistry: Reactions, Mechanisms and Structure, 4th Ed., pp. 1098–1099, 1184–1185 (John Wiley & Sons, N.Y. 1992).

Nikaido et al., Acid-Catalyzed Oxidation of Benzaldehydes to Phenols by Hydrogen Peroxide, *J. Org. Chem.*, vol. 49, pp. 4740–4741 (1984).

Olah et al., Formylating Agents, *Chemical Reviews*, vol. 87, No. 4, pp. 671–686 (1987).

Ohloff et al., Chemical Classification and Structure-Odour Relationships, Perfumes: Art, Science and Technology, pp. 287–330 (Amsterdam 1991).

Rahm et al., Acetone Cyanohydrin, A Convenient Formylation Reagent For Arenes, *Synthetic Communications*, vol. 12, No. 6, pp. 485–487 (1982).

Rieche et al., Aromatic Aldehydes. Mesitaldehyde, *Organic Syntheses*, Collective vol. 5, pp. 49–50 (1973).

Syper, The Baeyer-Villiger Oxidation of Aromatic Aldehydes and Ketones with Hydrogen Peroxide Catalyzed by Selenium Compounds, *Synthesis*, pp. 167–172 (1989).

Syper, Partial Oxidation of Aliphatic Side Chains With Oerium (IV), *Tetrahedron Letters*, No. 37, pp. 4493–4498 (1966).

Syper, Silver (II) As An Oxidant For Organic Compounds, *Tetrahedron Letters*, No. 42, pp. 4193–4198 (1967).

Theimer, Fragrance Chemistry: The Science of the Sense of Smell, pp. 509–534 (Academic Press 1982).

French Patent No. 1,392,804 (as reported in *Chemical Abstracts*, 29–Essential Oils and Cosmetics, vol. 63, p. 6781 (1965)).

Chastrette, Importance of Hydrogen Bonding in the Recognition of Musky Odours, ECRO VIII: Abstracts, pp. 176–177 (1987).

Perrier, *Chem. Ber.*, vol. 33, p. 815 et seq. (1990).

Perrier, *Bull. Soc. Chim. France*, p. 859 et seq. (1904).

ALKYL INDANE ALDEHYDE COMPOUNDS

RELATED APPLICATION

This application is a continuation-in-part of patent application U.S. Ser. No. 079,008, filed Jun. 18, 1993, now U.S. Pat. No. 5,292,720, the disclosures of which are hereby incorporated herein by reference in their entirety.

BACKGROUND OF THE INVENTION

The present invention relates, inter alia, to novel alkyl indane aldehyde compounds having fragrant musk-like aroma.

Musk has been a highly valued fragrance for decades, finding use in numerous products such as in perfumes, colognes, soaps, cosmetics, as well as others. Natural musk is obtained from the glands of the endangered tiny musk deer of Central Asia, *Moschus moschiferous*, commonly referred to as the Asian musk deer. Such natural musk, however, is extremely scarce and expensive. Accordingly, fragrance chemists around the world have spent considerable time and effort searching for synthetic products which duplicate or closely simulate the natural musk scent.

As a result of such research efforts, a number of different synthetic musks have been discovered. Among such synthetic compounds are the acetyl indanes described by Sprecker et al., U.S. Pat. No. 4,466,908, compounds of the formulas

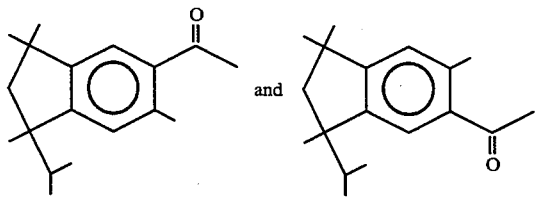

Similarly, Fehr et al., *Helvetica Chimica Acta*, Vol. 72, pp. 1537–1553 (1989) discusses such synthetic musks as those of the formula

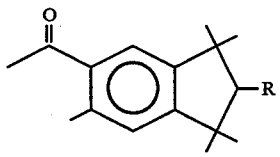

wherein R is either H or CH₃.

Traas et al., U.S. Pat. No. 4,352,748 discloses formylated and acetylated indane musks, including those of the formulas

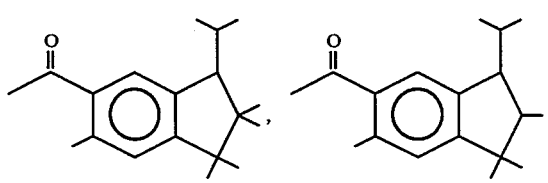

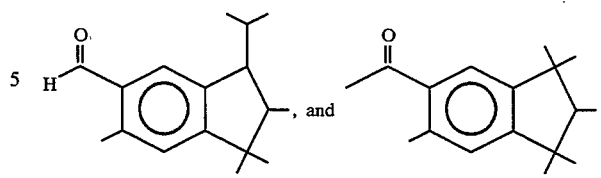

Other acetyl indanes, such as 6-acetyl-1,1,3,3,5-pentamethylindane, 5-acetyl-1,1,2,3,3-pentamethylindane and 6-acetyl-5-ethyl-1,1,2,3,3-pentamethylindane, are disclosed in French Patent No. 1,392,804 (as reported in Chemical Abstracts, Vol. 63, p. 1681d (1965)).

Cobb et al., U.S. Pat. No. 4,551,573, also discusses various indane compounds.

New and or better musk aroma compounds are needed to meet the demands of the fragrance industries. The present invention is directed to these, as well as other, important ends.

SUMMARY OF THE INVENTION

The present invention provides novel compounds of the formula [I]:

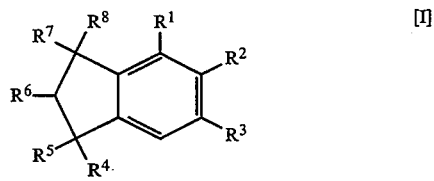

wherein
$R^1$ is H, $CH_3$, $CH_2CH_3$, $OCH_3$ or OH,
$R^2$ and $R^3$ are, independently, H, $CH_3$, $CH_2CH_3$, $OCH_3$, OH or C(O)H,
$R^4$ and $R^7$ are, independently, H, $CH_3$, $CH_2CH_3$ or $CH(CH_3)_2$,
$R^5$ and $R^8$ are, independently H or $CH_3$, and
$R^6$ is H, $CH_3$ or $CH_2CH_3$, provided that
(i) one of $R^2$ and $R^3$ is C(O)H, and one of $R^2$ and $R^3$ is other than C(O)H,
(ii) when $R^1$ is H, then $R^2$ and $R^3$ are other than $OCH_3$ or OH,
(iii) when $R^1$ is other than H, then $R^7$ is $CH_3$ or $CH_2CH_3$,
(iv) no more than one of $R^4$, $R^6$ and $R^7$ is $CH_2CH_3$ or $CH(CH_3)_2$,
(v) no more than one of $R^4$, $R^5$, $R^6$, $R^7$ and $R^8$ is H,
(vi) when each of $R^1$, $R^3$, $R^4$ and $R^5$ are $CH_3$, then $R^8$ is H,
(vii) when $R^4$ is $CH(CH_3)_2$, then at least one of $R^5$ or $R^6$ is H,
(viii) when $R^7$ is $CH(CH_3)_2$, then at least one of $R^6$ or $R^8$ is H,
(ix) when $R^1$ is $OCH_3$, then $R^2$ and $R^3$ are other than OH,
(x) when $R^1$ is OH, then $R^2$ and $R^3$ are other than OH or $OCH_3$,
(xi) when $R^1$ is H, $R^4$ is $CH(CH_3)_2$ and $R^5$ is $CH_3$, then one of $R^2$ and $R^3$ is $CH_2CH_3$,
(xii) when $R^1$ is H, $R^7$ is $CH(CH_3)_2$ and $R^8$ is $CH_3$, then one of $R^2$ and $R^3$ is $CH_2CH_3$,
(xiii) when $R^1$ is H, $R^7$ is $CH(CH_3)_2$ and $R^8$ is H, then $R^3$ is C(O)H, (xiv) when $R^1$ is H, $R^4$ is $CH(CH_3)_2$ and $R^5$ is H, then $R^2$ is C(O)H, (xv) when $R^1$ is H, $R^7$ is $CH_2CH_3$ and $R^4$, $R^5$ and $R^8$ are $CH_3$, then both of $R^2$ and $R^3$ are other than $CH_3$, when $R^1$ is H, $R^4$ is $CH_2CH_3$ and $R^5$, $R^7$ and $R^8$ are $CH_3$, then both of $R^2$ and $R^3$ are other than $CH_3$, and (xvii) when one of $R^2$ and $R^3$ is $CH_3$, and each of $R^4$, $R^5$, $R^6$, $R^7$ and $R^8$ are $CH_3$, then $R^1$ is other than H.

The foregoing compounds possess an active musk aroma having utility in the fragrance industry. The compounds of the invention may be used alone, or in combination with carriers, additional perfumery materials, and/or other ingredients, to provide various products, such as perfumes, colognes, soaps, and cosmetics.

DETAILED DESCRIPTION OF THE INVENTION

As noted above, the present invention is directed to novel musk compounds of the formula [I]:

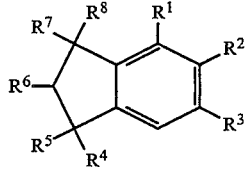

In the above formula [I], the R substituents may be selected as follows: $R^1$ may be selected from the group consisting of H, $CH_3$, $CH_2CH_3$, $OCH_3$ and OH; $R^2$ may be selected from the group consisting of H, $CH_3$, $CH_2CH_3$, $OCH_3$, OH and C(O)H; $R^3$ may be selected from the group consisting of H, $CH_3$, $CH_2CH_3$, $OCH_3$, OH and C(O)H; $R^4$ may be selected from the group consisting of H, $CH_3$, $CH_2CH_3$ and $CH(CH_3)_2$; $R^5$ may be selected from the group consisting of H and $CH_3$; $R^6$ may be selected from the group consisting of H, $CH_3$ and $CH_2CH_3$; $R^7$ may be selected from the group consisting of H, $CH_3$, $CH_2CH_3$ and $CH(CH_3)_2$; and $R^8$ may be selected from the group consisting of H and $CH_3$.

The foregoing selection of R substituents should, however, be made with the following qualifications in mind: that one of $R^2$ and $R^3$ is C(O)H, and the other of $R^2$ and $R^3$ is other than C(O)H; that when $R^1$ is H, then $R^2$ and $R^3$ are both other than $OCH_3$ or OH; that when $R^1$ is other than H, then $R^7$ is either $CH_3$ or $CH_2CH_3$; that no more than one of $R^4$, $R^6$ and $R^7$ is either $CH_2CH_3$ or $CH(CH_3)_2$; that no more than one of $R^4$, $R^5$, $R^6$, $R^7$ and $R^8$ is H; that when all of $R^1$, $R^3$, $R^4$ and $R^5$ are $CH_3$, then $R^8$ is H; that when $R^4$ is $CH(CH_3)_2$, then one or both of $R^5$ or $R^6$ is H; that when $R^7$ is $CH(CH_3)_2$, then one or both of $R^6$ or $R^8$ is H; that when $R^1$ is $OCH_3$, then $R^2$ and $R^3$ are both other than OH; that when $R^1$ is OH, then $R^2$ and $R^3$ are both other than either OH or $OCH_3$; that when all of the following is true—$R^1$ is H, $R^4$ is $CH(CH_3)_2$ and $R^5$ is $CH_3$—then one of $R^2$ and $R^3$ is $CH_2CH_3$; that when all of the following is true—$R^1$ is H, $R^7$ is $CH(CH_3)_2$ and $R^8$ is $CH_3$—then one of $R^2$ and $R^3$ is $CH_2CH_3$; that when all of the following is true—$R^1$ is H, $R^7$ is $CH(CH_3)_2$ and $R^8$ is H—then $R^3$ is C(O)H; that when all of the following is true—$R^1$ is H, $R^4$ is $CH(CH_3)_2$ and $R^5$ is H—then $R^2$ is C(O)H; that when all of the following is true—$R^1$ is H, $R^7$ is $CH_2CH_3$ and $R^4$, $R^5$ and $R^8$ are $CH_3$—then both of $R^2$ and $R^3$ are other than $CH_3$; that when all of the following is true—when $R^1$ is H, $R^4$ is $CH_2CH_3$ and $R^5$, $R^7$ and $R^8$ are $CH_3$—then both of $R^2$ and $R^3$ are other than $CH_3$; and that when all of the following is true—one of $R^2$ and $R^3$ is $CH_3$, and each of $R^4$, $R^5$, $R^6$, $R^7$ and $R^8$ are $CH_3$—then $R^1$ is other than H.

For reasons of their fragrance characteristics, synthesis advantages, formulation benefits, and/or other values, the following are preferable classes of compounds within the scope of Formula [I]:

Compounds of Formula [I] wherein $R^2$ is C(O)H.

Compounds of Formula [I] wherein at least one (that is, one or more) of $R^1$, $R^2$ and $R^3$ are, independently, $OCH_3$ or OH.

Compounds of Formula [I] wherein at least one (that is, one or more) of $R^1$, $R^2$ and $R^3$ are $OCH_3$.

Compounds of Formula [I] wherein $R^1$ is H, $CH_3$, $CH_2CH_3$ or $OCH_3$, and $R^2$ and $R^3$ are, independently, H, $CH_3$, $CH_2CH_3$, $OCH_3$ or C(O)H.

Compounds of Formula [I] wherein $R^1$ is H, $CH_3$ or $OCH_3$, and $R^2$ and $R^3$, independently, are H, $CH_3$, $OCH_3$ or C(O)H.

Compounds of Formula [I] wherein at least one (that is, one or more) of $R^4$ or $R^7$ are H, $CH_3$ or $CH_2CH_3$.

Compounds of Formula [I] wherein $R^4$ and $R^7$ are, independently, $CH_3$, $CH_2CH_3$ or $CH(CH_3)_2$, and $R^5$ and $R^8$ are $CH_3$.

Compounds of Formula [I] wherein $R^4$ and $R^7$ are, independently, $CH_3$, $CH_2CH_3$ or $CH(CH_3)_2$, $R^5$ and $R^8$ are $CH_3$ and $R^6$ is $CH_3$ or $CH_2CH_3$.

Compounds of Formula [I] wherein $R^4$ is $CH(CH_3)_2$.

Specific compounds of Formula [I] which are most preferred, for reasons of fragrance characteristics, synthesis advantages, formulation benefits, and/or other values are as follows:

The compound of Formula [I] wherein compound of Claim 1 wherein $R^1$ is $CH_3$, $R^2$ is C(O)H, $R^3$ is $OCH_3$, $R^4$ is $CH_3$, $R^5$ is $CH_3$, $R^6$ is $CH_3$, $R^7$ is $CH_3$ and $R^8$ is $CH_3$.

The compound of Formula [I] wherein $R^1$ is $OCH_3$, $R^2$ is C(O)H, $R^3$ is $CH_3$, $R^4$ is $CH_3$, $R^5$ is $CH_3$, $R^6$ is $CH_3$, $R^7$ is $CH_3$ and $R^8$ is $CH_3$.

The compound of Formula [I] wherein $R^1$ is $CH_3$, $R^2$ is C(O)H, $R^3$ is $CH_3$, $R^4$ is $CH_2CH_3$, $R^5$ is $CH_3$, $R^6$ is H, $R^7$ is $CH_3$ and $R^8$ is $CH_3$.

The compound of Formula [I] wherein $R^1$ is $CH_3$, $R^2$ is C(O)H, $R^3$ is $OCH_3$, $R^4$ is $CH_2CH_3$, $R^5$ is $CH_3$, $R^6$ is H, $R^7$ is $CH_3$ and $R^8$ is $CH_3$.

The compound of Formula [I] wherein $R^1$ is $CH_3$, $R^2$ is C(O)H, $R^3$ is $OCH_3$, $R^4$ is $CH_3$, $R^5$ is $CH_3$, $R^6$ is H, $R^7$ is $CH_2CH_3$ and $R^8$ is $CH_3$.

The compound of Formula [I] wherein $R^1$ is $OCH_3$, $R^2$ is C(O)H, $R^3$ is $CH_3$, $R^4$ is $CH_2CH_3$, $R^5$ is $CH_3$, $R^6$ is H, $R^7$ is $CH_3$ and $R^8$ is $CH_3$.

The compound of Formula [I] wherein $R^1$ is $OCH_3$, $R^2$ is C(O)H, $R^3$ is $CH_3$, $R^4$ is $CH_3$, $R^5$ is $CH_3$, $R^6$ is H, $R^7$ is $CH_2CH_3$ and $R^8$ is $CH_3$.

The compound of Formula [I] wherein $R^1$ is $CH_3$, $R^2$ is C(O)H, $R^3$ is $CH_3$, $R^4$ is $CH(CH_3)_2$, $R^5$ is H, $R^6$ is $CH_3$, $R^7$ is $CH_3$ and $R^8$ is $CH_3$.

The compound of Formula [I] wherein $R^1$ is $CH_3$, $R^2$ is C(O)H, $R^3$ is $OCH_3$, $R^4$ is $CH(CH_3)_2$, $R^5$ is H, $R^6$ is $CH_3$, $R^7$ is $CH_3$ and $R^8$ is $CH_3$.

The compound of Formula [I] wherein $R^1$ is $OCH_3$, $R^2$ is C(O)H, $R^3$ is $CH_3$, $R^4$ is $CH(CH_3)_2$, $R^5$ is H, $R^6$ is $CH_3$, $R^7$ is $CH_3$ and $R^8$ is $CH_3$.

The compound of Formula [I] wherein $R^1$ is $OCH_3$, $R^2$ is $C(O)H$, $R^3$ is $OCH_3$, $R^4$ is $CH(CH_3)_2$, $R^5$ is H, $R^6$ is $CH_3$, $R^7$ is $CH_3$ and $R^8$ is $CH_3$.

The compound of Formula [I] wherein $R^1$ is H, $R^2$ is $C(O)H$, $R^3$ is $CH_3$, $R^4$ is $CH(CH_3)_2$, $R^5$ is H, $R^6$ is $CH_3$, $R^7$ is $CH_3$ and $R^8$ is $CH_3$.

The novel alkyl indane aldehyde compounds of the present invention may be prepared in various fashions. In the preferable protocol, alkyl indanes are first prepared. Then the alkyl indanes are formylated (that is, the radical —C(O)H is added to the benzene ring of the indane structure, to form an alkylated indane aldehyde), or oxidized (that is, a —$CH_3$ substituent on the benzene ring of the indane structure is oxidized to —C(O)H, to form an alkyl indane aldehyde), yielding the alkyl indane aldehyde compounds of Formula [I]. Examples 1-6 illustrate specific methodology which may be utilized for the preparation of compounds of the present invention.

In general, alkyl indane compounds or alkyl indane aldehyde compounds may be prepared by numerous synthetic routes which will be readily apparent to those skilled in the art, once armed with the present disclosure. Examples of suitable methodology which may be employed or modified in accordance with the present invention to prepare such compounds include Fehr et al., U.S. Pat. Nos. 5,162,588, Cobb et al., 4,551,573, Gozenbach et al., 4,406,828, Traas et al., 4,352,748, Sprecker et al, 4,162,256, 4,466,908 and 4,652,400, Wood et al., 3,509,215, Stofberg et al., 3,278,622, Frank 5,095,152, 5,087,770, 5,087,785, and 5,206,217, DeSimone, 4,018,719, Fehr et al., *Helvetica Chimica Acta*, Vol. 72, pp. 1537-1553 (1989), European Patent Application Publication No. 0,393,742, Great Britain Patent No. 1,459,036, Japanese Patent No. SHO 50-40761, and French Patent No. 1,392,804 (also reported in Chemical Abstracts, Vol. 63, p. 1681d (1965), the disclosures of each of which are hereby incorporated herein by reference, in their entirety. Modifications of such methodology sufficient to enable preparation of the specific novel compounds of the present invention will be readily apparent to those skilled in the art once placed in possession of the present invention.

In accordance with Frank, U.S. Pat. Nos. 5,087,785 and 5,087,770, for example, alkyl indanes may be prepared by isomerizing an alkylated tetrahydronaphthalene in the presence of (i) a Lewis acid (the Lewis acid being present in an amount of less than about 50 mole percent based on the amount of the alkylated tetrahydronaphthalene), and (ii) a solvent which can be a halogenated or unhalogenated solvent and, optionally, (iii) a phase transfer agent. Exemplary Lewis acids include titanium chloride, aluminum chloride and aluminum bromide. Exemplary halogenated solvents include dichloromethane, trichloromethane and 1,2-dichloroethane, and exemplary unhalogenated solvents include cyclohexane. Exemplary phase transfer agents include methyltrioctylammonium chloride and a mixture of methyltrioctylammonium chloride and methyltridecylammonium chloride (marketed under the trademark ADOGEN-464 ™, by Sherex Co., Dublin, Ohio).

In the foregoing process, the molar proportions of the reagents can be varied over a relatively wide range, provided that the Lewis acid is present in an amount of less than about 50 mole percent based on the amount of the alkylated tetrahydronaphthalene starting material, the precise amounts of the reagents being dependent upon such factors as the particular solvent employed, the presence or absence of a phase transfer agent, and the specific tetrahydronaphthalene starting material and other reaction conditions such as time, temperature, pressure, etc. Suitable reagent amounts will be well within the ambit of those skilled in the art, once armed with the present disclosures.

Although, in general, the molar proportions of the reagents employed in the process may be relatively widely varied, for best results, however, it is important to maintain a ratio of less than one mole of phase transfer agent per mole of Lewis acid. Preferably, the molar ratio is about 0.8 to 1.0, more preferably about 0.5 to 1.0, phase transfer agent to Lewis acid.

The subject isomerization reaction may be carried out in any suitable vessel which provides sufficient contacting between the Lewis acid, the phase transfer agent and the other reactants. For simplicity, a stirred batch reactor can be employed. The reaction vessel used should be resistant to the possible corrosive nature of the Lewis acid, such as a glass-lined vessel. The reagents of the present process may be added to the vessel in any order, although generally the solvent, the alkylated tetrahydronaphthalene, and any phase transfer agent are added first, followed by Lewis acid addition. The reaction may be carried out over a wide temperature range, but is preferably carried out at temperatures from about 0° C. to about 20° C. The pressure at which the reaction is carried out and the type of atmosphere are not critical. Generally, the isomerization reaction proceeds to equilibrium in about 1 to about 8 hours.

Product can be recovered from the reaction mixture by first quenching the reaction mixture in cold water or on crushed ice, preferably on ice, and then processing the mixture in the usual manner for Friedel-Crafts reactions to extract the indane compounds. Suitable extraction protocol is described, for example, in George A. Olah, *Friedel-Crafts And Related Reactions*, Vols. 1 and 2 (Interscience Publishers, John Wiley and Sons, New York, N.Y. 1964), the disclosures of which are hereby incorporated by reference in their entirety. Typically, following quenching and the resultant phase separation, the organic layer is washed an additional time with water to aid in removal of the Lewis acid. One or more additional washings can be carried out with dilute alkali solution to further aid Lewis acid removal. The resultant product is generally a mixture of the alkylated tetrahydronaphthalene starting material and the desired secondary alkyl indane isomerates. A more purified product may be obtained by subjecting the washed reaction mixture to reduced pressure fractional distillation, commercial chromatographic separation or other separation means known to those skilled in the art.

Alkylated tetrahydronaphthalene starting materials may be obtained commercially, or prepared using numerous well known procedures including those disclosed in Frank, U.S. Pat. Nos. 4,877,911, 4,877,914, 4,877,910, 4,877,916, 4,877,915, 4,877,913 and 4,877,912, Cobb et al., 4,551,573, Japanese Patent No. SHO 57-40420, Wood, U.S. Pat. Nos. 3,246,044, Wood et al., 3,856,875, Sato et al., 4,284,818, Kahn, 3,379,785, Suzukamo et al., 4,767,882, the disclosures of each of which are hereby incorporated herein by reference, in their entirety.

Alkyl indane compounds may then be formylated or oxidized to form alkyl indane aldehydes using conventional formylation or oxidation technology, as will be readily apparent to those skilled in the art, once armed with the present disclosure.

For example, alkyl indane compounds may be formylated using the following formylation process. Specifically, to prepare alkyl indane aldehyde compounds of the present invention, the alkyl indanes may be preferably reacted with α,α-dichloromethyl methyl ether, in a solvent such as an organic solvent (preferably a halogenated organic solvent such as, for example, anhydrous dichloromethane), in the presence of a Lewis acid (preferably titanium chloride; $TiCl_4$). Other suitable halogenated solvents and Lewis acids are discussed above, and will be readily apparent to those skilled in the art, once armed with the present disclosures. In general, formylation methods are well known in the art and are described, for example, in *Organic Syntheses*, Collective Vol. 5, pp. 49–50, by A. Rieche, H. Gross, and E. Hoft, edited by H. E. Baumgarten, John Wiley and Sons (New York, N.Y. 1973), Rahm, *Synthetic Communications*, Vol. 12, No. 6, pp. 485–487 (1982), Effenberger, *Angewandte Chemie International Edition (English)*, Vol. 19, No. 3, pp. 151–230 (1980), Olah et al., *Chemical Reviews*, Vol. 87, No. 4, pp. 671–686 (1987), and Hauser et al., *Synthesis*, pp. 723–724 (August 1987), the disclosures of each of which are hereby incorporated herein by reference, in their entirety.

Alternatively, to prepare alkyl indane aldehydes from alkyl indanes using oxidation techniques, the alkyl indanes are preferably reacted with ceric ammonium nitrate $(Ce(NO_3)_4 \cdot NH_4NO_3)$, a strong oxidant for organic compounds, in the presence of acetic acid. In general, these and other suitable oxidation methods are well known in the art, and are described, for example, in Syper, *Tetrahedron Letters*, No. 37, pp. 4493–4498 (1966), Laing et al., *J. Chem. Soc.* (C), pp. 2915–2918 (1968), Imamoto et al., *Chemistry Letters*, pp. 1445–1446 (1990), Kreh et al., *Tetrahedron Letters*, Vol. 28, No. 10, pp. 1067–1068 (1987), Hauser et al., *Communications*, pp. 72–73 (August 1987), and Syper, *Tetrahedron Letters*, No. 42, pp. 4193–4198 (1967).

Further purification of the alkyl indane aldehyde compounds of Formula [I] may be carried out, if desired, using, for example, standard fractional distillation techniques, as well as other conventional extraction, distillation, crystallization and chromatography techniques, and the like.

Exemplary alkyl indane aldehyde compounds are shown in Table I below.

TABLE I

| Compound | $R^1$ | $R^2$ | $R^3$ | $R^4$ | $R^5$ | $R^6$ | $R^7$ | $R^8$ |
|---|---|---|---|---|---|---|---|---|
| 1 | H | H | C(O)H | H | $CH_3$ | $CH_3$ | $CH_3$ | $CH_3$ |
| 2 | H | H | C(O)H | H | $CH_3$ | $CH_3$ | $CH_2CH_3$ | $CH_3$ |
| 3 | H | H | C(O)H | H | $CH_3$ | $CH_2CH_3$ | $CH_3$ | $CH_3$ |
| 4 | H | H | C(O)H | $CH_3$ | $CH_3$ | H | $CH_3$ | $CH_3$ |
| 5 | H | H | C(O)H | $CH_3$ | $CH_3$ | H | $CH_2CH_3$ | $CH_3$ |
| 6 | H | H | C(O)H | $CH_3$ | $CH_3$ | $CH_3$ | H | $CH_3$ |
| 7 | H | H | C(O)H | $CH_3$ | $CH_3$ | $CH_2CH_3$ | H | $CH_3$ |
| 8 | H | H | C(O)H | $CH_3$ | $CH_3$ | $CH_3$ | $CH_2CH_3$ | H |
| 9 | H | H | C(O)H | $CH_3$ | $CH_3$ | $CH_3$ | $CH(CH_3)_2$ | H |
| 10 | H | H | C(O)H | $CH_3$ | $CH_3$ | $CH_2CH_3$ | $CH_3$ | H |
| 11 | H | H | C(O)H | $CH_2CH_3$ | H | $CH_3$ | $CH_3$ | $CH_3$ |
| 12 | H | H | C(O)H | $CH_2CH_3$ | $CH_3$ | H | $CH_3$ | $CH_3$ |
| 13 | H | H | C(O)H | $CH_2CH_3$ | $CH_3$ | $CH_3$ | H | $CH_3$ |
| 14 | H | H | C(O)H | $CH(CH_3)_2$ | H | $CH_3$ | $CH_3$ | $CH_3$ |
| 15 | H | $CH_3$ | C(O)H | H | $CH_3$ | $CH_3$ | $CH_3$ | $CH_3$ |
| 16 | H | $CH_3$ | C(O)H | H | $CH_3$ | $CH_3$ | $CH_2CH_3$ | $CH_3$ |
| 17 | H | $CH_3$ | C(O)H | H | $CH_3$ | $CH_2CH_3$ | $CH_3$ | $CH_3$ |
| 18 | H | $CH_3$ | C(O)H | $CH_3$ | $CH_3$ | H | $CH_3$ | $CH_3$ |
| 19 | H | $CH_3$ | C(O)H | $CH_3$ | $CH_3$ | H | $CH_2CH_3$ | $CH_3$ |
| 20 | H | $CH_3$ | C(O)H | $CH_3$ | $CH_3$ | $CH_3$ | H | $CH_3$ |
| 21 | H | $CH_3$ | C(O)H | $CH_3$ | $CH_3$ | $CH_2CH_3$ | H | $CH_3$ |
| 22 | H | $CH_3$ | C(O)H | $CH_3$ | $CH_3$ | $CH_3$ | $CH_2CH_3$ | H |
| 23 | H | $CH_3$ | C(O)H | $CH_3$ | $CH_3$ | $CH_3$ | $CH(CH_3)_2$ | H |
| 24 | H | $CH_3$ | C(O)H | $CH_2CH_3$ | H | $CH_3$ | $CH_3$ | $CH_3$ |
| 25 | H | $CH_3$ | C(O)H | $CH_2CH_3$ | $CH_3$ | $CH_3$ | H | $CH_3$ |
| 26 | H | $CH_3$ | C(O)H | $CH(CH_3)_2$ | H | $CH_3$ | $CH_3$ | $CH_3$ |
| 27 | H | $CH_2CH_3$ | C(O)H | H | $CH_3$ | $CH_3$ | $CH_3$ | $CH_3$ |
| 28 | H | $CH_2CH_3$ | C(O)H | H | $CH_3$ | $CH_3$ | $CH_2CH_3$ | $CH_3$ |
| 29 | H | $CH_2CH_3$ | C(O)H | H | $CH_3$ | $CH_2CH_3$ | $CH_3$ | $CH_3$ |
| 30 | H | $CH_2CH_3$ | C(O)H | $CH_3$ | $CH_3$ | H | $CH_3$ | $CH_3$ |
| 31 | H | $CH_2CH_3$ | C(O)H | $CH_3$ | $CH_3$ | H | $CH_2CH_3$ | $CH_3$ |
| 32 | H | $CH_2CH_3$ | C(O)H | $CH_3$ | $CH_3$ | H | $CH(CH_3)_2$ | $CH_3$ |
| 33 | H | $CH_2CH_3$ | C(O)H | $CH_3$ | $CH_3$ | $CH_3$ | H | $CH_3$ |
| 34 | H | $CH_2CH_3$ | C(O)H | $CH_3$ | $CH_3$ | $CH_2CH_3$ | H | $CH_3$ |
| 35 | H | $CH_2CH_3$ | C(O)H | $CH_3$ | $CH_3$ | $CH_3$ | $CH_2CH_3$ | H |
| 36 | H | $CH_2CH_3$ | C(O)H | $CH_3$ | $CH_3$ | $CH_3$ | $CH(CH_3)_2$ | H |
| 37 | H | $CH_2CH_3$ | C(O)H | $CH_2CH_3$ | H | $CH_3$ | $CH_3$ | $CH_3$ |
| 38 | H | $CH_2CH_3$ | C(O)H | $CH_2CH_3$ | $CH_3$ | H | $CH_3$ | $CH_3$ |
| 39 | H | $CH_2CH_3$ | C(O)H | $CH_2CH_3$ | $CH_3$ | $CH_3$ | H | $CH_3$ |
| 40 | H | $CH_2CH_3$ | C(O)H | $CH(CH_3)_2$ | H | $CH_3$ | $CH_3$ | $CH_3$ |
| 41 | H | $CH_2CH_3$ | C(O)H | $CH(CH_3)_2$ | $CH_3$ | H | $CH_3$ | $CH_3$ |
| 42 | $CH_3$ | H | C(O)H | H | $CH_3$ | $CH_3$ | $CH_3$ | $CH_3$ |
| 43 | $CH_3$ | H | C(O)H | H | $CH_3$ | $CH_3$ | $CH_2CH_3$ | $CH_3$ |
| 44 | $CH_3$ | H | C(O)H | H | $CH_3$ | $CH_2CH_3$ | $CH_3$ | $CH_3$ |
| 45 | $CH_3$ | H | C(O)H | $CH_3$ | $CH_3$ | H | $CH_3$ | $CH_3$ |
| 46 | $CH_3$ | H | C(O)H | $CH_3$ | $CH_3$ | H | $CH_2CH_3$ | $CH_3$ |
| 47 | $CH_3$ | H | C(O)H | $CH_3$ | $CH_3$ | $CH_3$ | $CH_3$ | H |
| 48 | $CH_3$ | H | C(O)H | $CH_3$ | $CH_3$ | $CH_3$ | $CH_2CH_3$ | H |
| 49 | $CH_3$ | H | C(O)H | $CH_3$ | $CH_3$ | $CH_2CH_3$ | $CH_3$ | H |
| 50 | $CH_3$ | H | C(O)H | $CH_2CH_3$ | H | $CH_3$ | $CH_3$ | $CH_3$ |
| 51 | $CH_3$ | H | C(O)H | $CH_2CH_3$ | $CH_3$ | H | $CH_3$ | $CH_3$ |

TABLE I-continued

| Compound | R¹ | R² | R³ | R⁴ | R⁵ | R⁶ | R⁷ | R⁸ |
|---|---|---|---|---|---|---|---|---|
| 52 | CH₃ | H | C(O)H | CH₂CH₃ | CH₃ | CH₃ | CH₃ | H |
| 53 | CH₃ | H | C(O)H | CH(CH₃)₂ | H | CH₃ | CH₃ | CH₃ |
| 54 | CH₃ | H | C(O)H | CH(CH₃)₂ | CH₃ | H | CH₃ | CH₃ |
| 55 | CH₃ | CH₃ | C(O)H | H | CH₃ | CH₃ | CH₃ | CH₃ |
| 56 | CH₃ | CH₃ | C(O)H | H | CH₃ | CH₃ | CH₂CH₃ | CH₃ |
| 57 | CH₃ | CH₃ | C(O)H | H | CH₃ | CH₂CH₃ | CH₃ | CH₃ |
| 58 | CH₃ | CH₃ | C(O)H | CH₃ | CH₃ | H | CH₃ | CH₃ |
| 59 | CH₃ | CH₃ | C(O)H | CH₃ | CH₃ | H | CH₂CH₃ | CH₃ |
| 60 | CH₃ | CH₃ | C(O)H | CH₃ | CH₃ | CH₃ | CH₃ | H |
| 61 | CH₃ | CH₃ | C(O)H | CH₃ | CH₃ | CH₃ | CH₂CH₃ | H |
| 62 | CH₃ | CH₃ | C(O)H | CH₃ | CH₃ | CH₂CH₃ | CH₃ | H |
| 63 | CH₃ | CH₃ | C(O)H | CH₂CH₃ | H | CH₃ | CH₃ | CH₃ |
| 64 | CH₃ | CH₃ | C(O)H | CH₂CH₃ | CH₃ | H | CH₃ | CH₃ |
| 65 | CH₃ | CH₃ | C(O)H | CH₂CH₃ | CH₃ | CH₃ | CH₃ | H |
| 66 | CH₃ | CH₃ | C(O)H | CH(CH₃)₂ | H | CH₃ | CH₃ | CH₃ |
| 67 | CH₃ | CH₃ | C(O)H | CH(CH₃)₂ | CH₃ | H | CH₃ | CH₃ |
| 68 | CH₃ | CH₂CH₃ | C(O)H | H | CH₃ | CH₃ | CH₃ | CH₃ |
| 69 | CH₃ | CH₂CH₃ | C(O)H | H | CH₃ | CH₃ | CH₂CH₃ | CH₃ |
| 70 | CH₃ | CH₂CH₃ | C(O)H | H | CH₃ | CH₂CH₃ | CH₃ | CH₃ |
| 71 | CH₃ | CH₂CH₃ | C(O)H | CH₃ | CH₃ | H | CH₃ | CH₃ |
| 72 | CH₃ | CH₂CH₃ | C(O)H | CH₃ | CH₃ | H | CH₂CH₃ | CH₃ |
| 73 | CH₃ | CH₂CH₃ | C(O)H | CH₃ | CH₃ | CH₃ | CH₃ | H |
| 74 | CH₃ | CH₂CH₃ | C(O)H | CH₃ | CH₃ | CH₃ | CH₂CH₃ | H |
| 75 | CH₃ | CH₂CH₃ | C(O)H | CH₃ | CH₃ | CH₂CH₃ | CH₃ | H |
| 76 | CH₃ | CH₂CH₃ | C(O)H | CH₂CH₃ | H | CH₃ | CH₃ | CH₃ |
| 77 | CH₃ | CH₂CH₃ | C(O)H | CH₂CH₃ | CH₃ | H | CH₃ | CH₃ |
| 78 | CH₃ | CH₂CH₃ | C(O)H | CH₂CH₃ | CH₃ | CH₃ | CH₃ | H |
| 79 | CH₃ | CH₂CH₃ | C(O)H | CH(CH₃)₂ | H | CH₃ | CH₃ | CH₃ |
| 80 | CH₃ | CH₂CH₃ | C(O)H | CH(CH₃)₂ | CH₃ | H | CH₃ | CH₃ |
| 81 | CH₃ | C(O)H | H | H | CH₃ | CH₃ | CH₃ | CH₃ |
| 82 | CH₃ | C(O)H | H | H | CH₃ | CH₃ | CH₂CH₃ | CH₃ |
| 83 | CH₃ | C(O)H | H | H | CH₃ | CH₂CH₃ | CH₃ | CH₃ |
| 84 | CH₃ | C(O)H | H | CH₃ | CH₃ | H | CH₃ | CH₃ |
| 85 | CH₃ | C(O)H | H | CH₃ | CH₃ | H | CH₂CH₃ | CH₃ |
| 86 | CH₃ | C(O)H | H | CH₃ | CH₃ | CH₃ | CH₃ | H |
| 87 | CH₃ | C(O)H | H | CH₃ | CH₃ | CH₃ | CH₂CH₃ | H |
| 88 | CH₃ | C(O)H | H | CH₃ | CH₃ | CH₂CH₃ | CH₃ | H |
| 89 | CH₃ | C(O)H | H | CH₂CH₃ | H | CH₃ | CH₃ | CH₃ |
| 90 | CH₃ | C(O)H | H | CH₂CH₃ | CH₃ | H | CH₃ | CH₃ |
| 91 | CH₃ | C(O)H | H | CH₂CH₃ | CH₃ | CH₃ | CH₃ | H |
| 92 | CH₃ | C(O)H | H | CH(CH₃)₂ | H | CH₃ | CH₃ | CH₃ |
| 93 | CH₃ | C(O)H | H | CH(CH₃)₂ | CH₃ | H | CH₃ | CH₃ |
| 94 | CH₃ | C(O)H | CH₃ | H | CH₃ | CH₃ | CH₃ | CH₃ |
| 95 | CH₃ | C(O)H | CH₃ | H | CH₃ | CH₃ | CH₂CH₃ | CH₃ |
| 96 | CH₃ | C(O)H | CH₃ | H | CH₃ | CH₂CH₃ | CH₃ | CH₃ |
| 97 | CH₃ | C(O)H | CH₃ | CH₃ | CH₃ | CH₃ | CH₃ | H |
| 98 | CH₃ | C(O)H | CH₃ | CH₃ | CH₃ | CH₃ | CH₂CH₃ | H |
| 99 | CH₃ | C(O)H | CH₃ | CH₃ | CH₃ | CH₂CH₃ | CH₃ | H |
| 100 | CH₃ | C(O)H | CH₃ | CH₂CH₃ | H | CH₃ | CH₃ | CH₃ |
| 101 | CH₃ | C(O)H | CH₃ | CH₂CH₃ | CH₃ | H | CH₃ | CH₃ |
| 102 | CH₃ | C(O)H | CH₃ | CH₂CH₃ | CH₃ | CH₃ | CH₃ | H |
| 103 | CH₃ | C(O)H | CH₃ | CH(CH₃)₂ | H | CH₃ | CH₃ | CH₃ |
| 104 | CH₃ | C(O)H | CH₃ | CH(CH₃)₂ | CH₃ | H | CH₃ | CH₃ |
| 105 | CH₃ | C(O)H | CH₂CH₃ | H | CH₃ | CH₃ | CH₃ | CH₃ |
| 106 | CH₃ | C(O)H | CH₂CH₃ | H | CH₃ | CH₃ | CH₂CH₃ | CH₃ |
| 107 | CH₃ | C(O)H | CH₂CH₃ | H | CH₃ | CH₂CH₃ | CH₃ | CH₃ |
| 108 | CH₃ | C(O)H | CH₂CH₃ | CH₃ | CH₃ | H | CH₃ | CH₃ |
| 109 | CH₃ | C(O)H | CH₂CH₃ | CH₃ | CH₃ | H | CH₂CH₃ | CH₃ |
| 110 | CH₃ | C(O)H | CH₂CH₃ | CH₃ | CH₃ | CH₃ | CH₃ | H |
| 111 | CH₃ | C(O)H | CH₂CH₃ | CH₃ | CH₃ | CH₃ | CH₂CH₃ | H |
| 112 | CH₃ | C(O)H | CH₂CH₃ | CH₃ | CH₃ | CH₂CH₃ | CH₃ | H |
| 113 | CH₃ | C(O)H | CH₂CH₃ | CH₂CH₃ | H | CH₃ | CH₃ | CH₃ |
| 114 | CH₃ | C(O)H | CH₂CH₃ | CH₂CH₃ | CH₃ | H | CH₃ | CH₃ |
| 115 | CH₃ | C(O)H | CH₂CH₃ | CH₂CH₃ | CH₃ | CH₃ | CH₃ | H |
| 116 | CH₃ | C(O)H | CH₂CH₃ | CH(CH₃)₂ | H | CH₃ | CH₃ | CH₃ |
| 117 | CH₃ | C(O)H | CH₂CH₃ | CH(CH₃)₂ | CH₃ | H | CH₃ | CH₃ |
| 118 | CH₂CH₃ | H | C(O)H | H | CH₃ | CH₃ | CH₃ | CH₃ |
| 119 | CH₂CH₃ | H | C(O)H | H | CH₃ | CH₃ | CH₂CH₃ | CH₃ |
| 120 | CH₂CH₃ | H | C(O)H | H | CH₃ | CH₂CH₃ | CH₃ | CH₃ |
| 121 | CH₂CH₃ | H | C(O)H | CH₃ | CH₃ | H | CH₃ | CH₃ |
| 122 | CH₂CH₃ | H | C(O)H | CH₃ | CH₃ | H | CH₂CH₃ | CH₃ |
| 123 | CH₂CH₃ | H | C(O)H | CH₃ | CH₃ | CH₃ | CH₃ | H |
| 124 | CH₂CH₃ | H | C(O)H | CH₃ | CH₃ | CH₃ | CH₂CH₃ | H |
| 125 | CH₂CH₃ | H | C(O)H | CH₃ | CH₃ | CH₂CH₃ | CH₃ | H |
| 126 | CH₂CH₃ | H | C(O)H | CH₂CH₃ | H | CH₃ | CH₃ | CH₃ |
| 127 | CH₂CH₃ | H | C(O)H | CH₂CH₃ | CH₃ | H | CH₃ | CH₃ |
| 128 | CH₂CH₃ | H | C(O)H | CH₂CH₃ | CH₃ | CH₃ | CH₃ | H |
| 129 | CH₂CH₃ | H | C(O)H | CH(CH₃)₂ | H | CH₃ | CH₃ | CH₃ |
| 130 | CH₂CH₃ | H | C(O)H | CH(CH₃)₂ | CH₃ | H | CH₃ | CH₃ |
| 131 | CH₂CH₃ | CH₃ | C(O)H | H | CH₃ | CH₃ | CH₃ | CH₃ |
| 132 | CH₂CH₃ | CH₃ | C(O)H | H | CH₃ | CH₃ | CH₂CH₃ | CH₃ |

TABLE I-continued

| Compound | R¹ | R² | R³ | R⁴ | R⁵ | R⁶ | R⁷ | R⁸ |
|---|---|---|---|---|---|---|---|---|
| 133 | CH₂CH₃ | CH₃ | C(O)H | H | CH₃ | CH₂CH₃ | CH₃ | CH₃ |
| 134 | CH₂CH₃ | CH₃ | C(O)H | CH₃ | CH₃ | H | CH₃ | CH₃ |
| 135 | CH₂CH₃ | CH₃ | C(O)H | CH₃ | CH₃ | H | CH₂CH₃ | CH₃ |
| 136 | CH₂CH₃ | CH₃ | C(O)H | CH₃ | CH₃ | CH₃ | CH₃ | H |
| 137 | CH₂CH₃ | CH₃ | C(O)H | CH₃ | CH₃ | CH₃ | CH₂CH₃ | H |
| 138 | CH₂CH₃ | CH₃ | C(O)H | CH₃ | CH₃ | CH₂CH₃ | CH₃ | H |
| 139 | CH₂CH₃ | CH₃ | C(O)H | CH₂CH₃ | H | CH₃ | CH₃ | CH₃ |
| 140 | CH₂CH₃ | CH₃ | C(O)H | CH₂CH₃ | CH₃ | H | CH₃ | CH₃ |
| 141 | CH₂CH₃ | CH₃ | C(O)H | CH₂CH₃ | CH₃ | CH₃ | CH₃ | H |
| 142 | CH₂CH₃ | CH₃ | C(O)H | CH(CH₃)₂ | H | CH₃ | CH₃ | CH₃ |
| 143 | CH₂CH₃ | CH₃ | C(O)H | CH(CH₃)₂ | CH₃ | H | CH₃ | CH3 |
| 144 | CH₂CH₃ | CH₂CH₃ | C(O)H | H | CH₃ | CH₃ | CH₃ | CH₃ |
| 145 | CH₂CH₃ | CH₂CH₃ | C(O)H | H | CH₃ | CH₃ | CH₂CH₃ | CH₃ |
| 146 | CH₂CH₃ | CH₂CH₃ | C(O)H | H | CH₃ | CH₂CH₃ | CH₃ | CH₃ |
| 147 | CH₂CH₃ | CH₂CH₃ | C(O)H | CH₃ | CH₃ | H | CH₃ | CH₃ |
| 148 | CH₂CH₃ | CH₂CH₃ | C(O)H | CH₃ | CH₃ | H | CH₂CH₃ | CH₃ |
| 149 | CH₂CH₃ | CH₂CH₃ | C(O)H | CH₃ | CH₃ | CH₃ | CH₃ | H |
| 150 | CH₂CH₃ | CH₂CH₃ | C(O)H | CH₃ | CH₃ | CH₃ | CH₂CH₃ | H |
| 151 | CH₂CH₃ | CH₂CH₃ | C(O)H | CH₃ | CH₃ | CH₂CH₃ | CH₃ | H |
| 152 | CH₂CH₃ | CH₂CH₃ | C(O)H | CH₂CH₃ | H | CH₃ | CH₃ | CH₃ |
| 153 | CH₂CH₃ | CH₂CH₃ | C(O)H | CH₂CH₃ | CH₃ | H | CH₃ | CH₃ |
| 154 | CH₂CH₃ | CH₂CH₃ | C(O)H | CH₂CH₃ | CH₃ | CH₃ | CH₃ | H |
| 155 | CH₂CH₃ | CH₂CH₃ | C(O)H | CH(CH₃)₂ | H | CH₃ | CH₃ | CH₃ |
| 156 | CH₂CH₃ | CH₂CH₃ | C(O)H | CH(CH₃)₂ | CH₃ | H | CH₃ | CH₃ |
| 157 | CH₂CH₃ | C(O)H | H | H | CH₃ | CH₃ | CH₃ | CH₃ |
| 158 | CH₂CH₃ | C(O)H | H | H | CH₃ | CH₃ | CH₂CH₃ | CH₃ |
| 159 | CH₂CH₃ | C(O)H | H | H | CH₃ | CH₂CH₃ | CH₃ | CH₃ |
| 160 | CH₂CH₃ | C(O)H | H | CH₃ | CH₃ | H | CH₃ | CH₃ |
| 161 | CH₂CH₃ | C(O)H | H | CH₃ | CH₃ | H | CH₂CH₃ | CH₃ |
| 162 | CH₂CH₃ | C(O)H | H | CH₃ | CH₃ | CH₃ | CH₃ | H |
| 163 | CH₂CH₃ | C(O)H | H | CH₃ | CH₃ | CH₃ | CH₂CH₃ | H |
| 164 | CH₂CH₃ | C(O)H | H | CH₃ | CH₃ | CH₂CH₃ | CH₃ | H |
| 165 | CH₂CH₃ | C(O)H | H | CH₂CH₃ | H | CH₃ | CH₃ | CH₃ |
| 166 | CH₂CH₃ | C(O)H | H | CH₂CH₃ | CH₃ | H | CH₃ | CH₃ |
| 167 | CH₂CH₃ | C(O)H | H | CH₂CH₃ | CH₃ | CH₃ | CH₃ | H |
| 168 | CH₂CH₃ | C(O)H | H | CH(CH₃)₂ | H | CH₃ | CH₃ | CH₃ |
| 169 | CH₂CH₃ | C(O)H | H | CH(CH₃)₂ | CH₃ | H | CH₃ | CH₃ |
| 170 | CH₂CH₃ | C(O)H | CH₃ | H | CH₃ | CH₃ | CH₃ | CH₃ |
| 171 | CH₂CH₃ | C(O)H | CH₃ | H | CH₃ | CH₃ | CH₂CH₃ | CH₃ |
| 172 | CH₂CH₃ | C(O)H | CH₃ | H | CH₃ | CH₂CH₃ | CH₃ | CH₃ |
| 173 | CH₂CH₃ | C(O)H | CH₃ | CH₃ | CH₃ | H | CH₃ | CH₃ |
| 174 | CH₂CH₃ | C(O)H | CH₃ | CH₃ | CH₃ | H | CH₂CH₃ | CH₃ |
| 175 | CH₂CH₃ | C(O)H | CH₃ | CH₃ | CH₃ | CH₃ | CH₃ | H |
| 176 | CH₂CH₃ | C(O)H | CH₃ | CH₃ | CH₃ | CH₃ | CH₂CH₃ | H |
| 177 | CH₂CH₃ | C(O)H | CH₃ | CH₃ | CH₃ | CH₂CH₃ | CH₃ | H |
| 178 | CH₂CH₃ | C(O)H | CH₃ | CH₂CH₃ | H | CH₃ | CH₃ | CH₃ |
| 179 | CH₂CH₃ | C(O)H | CH₃ | CH₂CH₃ | CH₃ | H | CH₃ | CH₃ |
| 180 | CH₂CH₃ | C(O)H | CH₃ | CH₂CH₃ | CH₃ | CH₃ | CH₃ | H |
| 181 | CH₂CH₃ | C(O)H | CH₃ | CH(CH₃)₂ | H | CH₃ | CH₃ | CH₃ |
| 182 | CH₂CH₃ | C(O)H | CH₃ | CH(CH₃)₂ | CH₃ | H | CH₃ | CH₃ |
| 183 | CH₂CH₃ | C(O)H | CH₂CH₃ | H | CH₃ | CH₃ | CH₃ | CH₃ |
| 184 | CH₂CH₃ | C(O)H | CH₂CH₃ | H | CH₃ | CH₃ | CH₂CH₃ | CH₃ |
| 185 | CH₂CH₃ | C(O)H | CH₂CH₃ | H | CH₃ | CH₂CH₃ | CH₃ | CH₃ |
| 186 | CH₂CH₃ | C(O)H | CH₂CH₃ | CH₃ | CH₃ | H | CH₃ | CH₃ |
| 187 | CH₂CH₃ | OC(O)H | CH₂CH₃ | CH₃ | CH₃ | H | CH₂CH₃ | CH₃ |
| 188 | CH₂CH₃ | C(O)H | CH₂CH₃ | CH₃ | CH₃ | CH₃ | CH₃ | H |
| 189 | CH₂CH₃ | C(O)H | CH₂CH₃ | CH₃ | CH₃ | CH₃ | CH₂CH₃ | H |
| 190 | CH₂CH₃ | C(O)H | CH₂CH₃ | CH₃ | CH₃ | CH₂CH₃ | CH₃ | H |
| 191 | CH₂CH₃ | C(O)H | CH₂CH₃ | CH₂CH₃ | H | CH₃ | CH₃ | CH₃ |
| 192 | CH₂CH₃ | C(O)H | CH₂CH₃ | CH₂CH₃ | CH₃ | H | CH₃ | CH₃ |
| 193 | CH₂CH₃ | C(O)H | CH₂CH₃ | CH₂CH₃ | CH₃ | CH₃ | CH₃ | H |
| 194 | CH₂CH₃ | C(O)H | CH₂CH₃ | CH(CH₃)₂ | H | CH₃ | CH₃ | CH₃ |
| 195 | CH₂CH₃ | C(O)H | CH₂CH₃ | CH(CH₃)₂ | CH₃ | H | CH₃ | CH₃ |
| 196 | OCH₃ | H | C(O)H | H | CH₃ | CH₃ | CH₃ | CH₃ |
| 197 | OCH₃ | H | C(O)H | H | CH₃ | CH₃ | CH₂CH₃ | CH₃ |
| 198 | OCH₃ | H | C(O)H | H | CH₃ | CH₂CH₃ | CH₃ | CH₃ |
| 199 | OCH₃ | H | C(O)H | CH₃ | CH₃ | H | CH₃ | CH₃ |
| 200 | OCH₃ | H | C(O)H | CH₃ | CH₃ | H | CH₂CH₃ | CH₃ |
| 201 | OCH₃ | H | C(O)H | CH₃ | CH₃ | CH₃ | CH₃ | H |
| 202 | OCH₃ | H | C(O)H | CH₃ | CH₃ | CH₃ | CH₂CH₃ | H |
| 203 | OCH₃ | H | C(O)H | CH₃ | CH₃ | CH₂CH₃ | CH₃ | H |
| 204 | OCH₃ | H | C(O)H | CH₂CH₃ | H | CH₃ | CH₃ | CH₃ |
| 205 | OCH₃ | H | C(O)H | CH₂CH₃ | CH₃ | H | CH₃ | CH₃ |
| 206 | OCH₃ | H | C(O)H | CH₂CH₃ | CH₃ | CH₃ | CH₃ | H |
| 207 | OCH₃ | H | C(O)H | CH(CH₃)₂ | H | CH₃ | CH₃ | CH₃ |
| 208 | OCH₃ | H | C(O)H | CH(CH₃)₂ | CH₃ | H | CH₃ | CH₃ |
| 209 | OCH₃ | CH₃ | C(O)H | H | CH₃ | CH₃ | CH₃ | CH₃ |
| 210 | OCH₃ | CH₃ | C(O)H | H | CH₃ | CH₃ | CH₂CH₃ | CH₃ |
| 211 | OCH₃ | CH₃ | C(O)H | H | CH₃ | CH₂CH₃ | CH₃ | CH₃ |
| 212 | OCH₃ | CH₃ | C(O)H | CH₃ | CH₃ | H | CH₃ | CH₃ |
| 213 | OCH₃ | CH₃ | C(O)H | CH₃ | CH₃ | H | CH₂CH₃ | CH₃ |

TABLE I-continued

| Compound | R¹ | R² | R³ | R⁴ | R⁵ | R⁶ | R⁷ | R⁸ |
|---|---|---|---|---|---|---|---|---|
| 214 | OCH₃ | CH₃ | C(O)H | CH₃ | CH₃ | CH₃ | CH₃ | H |
| 215 | OCH₃ | CH₃ | C(O)H | CH₃ | CH₃ | CH₃ | CH₂CH₃ | H |
| 216 | OCH₃ | CH₃ | C(O)H | CH₃ | CH₃ | CH₂CH₃ | CH₃ | H |
| 217 | OCH₃ | CH₃ | C(O)H | CH₂CH₃ | H | CH₃ | CH₃ | CH₃ |
| 218 | OCH₃ | CH₃ | C(O)H | CH₂CH₃ | CH₃ | H | CH₃ | CH₃ |
| 219 | OCH₃ | CH₃ | C(O)H | CH₂CH₃ | CH₃ | CH₃ | CH₃ | H |
| 220 | OCH₃ | CH₃ | C(O)H | CH(CH₃)₂ | H | CH₃ | CH₃ | CH₃ |
| 221 | OCH₃ | CH₃ | C(O)H | CH(CH₃)₂ | CH₃ | H | CH₃ | CH₃ |
| 222 | OCH₃ | CH₂CH₃ | C(O)H | H | CH₃ | CH₃ | CH₃ | CH₃ |
| 223 | OCH₃ | CH₂CH₃ | C(O)H | H | CH₃ | CH₃ | CH₂CH₃ | CH₃ |
| 224 | OCH₃ | CH₂CH₃ | C(O)H | H | CH₃ | CH₂CH₃ | CH₃ | CH₃ |
| 225 | OCH₃ | CH₂CH₃ | C(O)H | CH₃ | CH₃ | H | CH₃ | CH₃ |
| 226 | OCH₃ | CH₂CH₃ | C(O)H | CH₃ | CH₃ | H | CH₂CH₃ | CH₃ |
| 227 | OCH₃ | CH₂CH₃ | C(O)H | CH₃ | CH₃ | CH₃ | CH₃ | H |
| 228 | OCH₃ | CH₂CH₃ | C(O)H | CH₃ | CH₃ | CH₃ | CH₂CH₃ | H |
| 229 | OCH₃ | CH₂CH₃ | C(O)H | CH₃ | CH₃ | CH₂CH₃ | CH₃ | H |
| 230 | OCH₃ | CH₂CH₃ | C(O)H | CH₂CH₃ | H | CH₃ | CH₃ | CH₃ |
| 231 | OCH₃ | CH₂CH₃ | C(O)H | CH₂CH₃ | CH₃ | H | CH₃ | CH₃ |
| 232 | OCH₃ | CH₂CH₃ | C(O)H | CH₂CH₃ | CH₃ | CH₃ | CH₃ | H |
| 233 | OCH₃ | CH₂CH₃ | C(O)H | CH(CH₃)₂ | H | CH₃ | CH₃ | CH₃ |
| 234 | OCH₃ | CH₂CH₃ | C(O)H | CH(CH₃)₂ | CH₃ | H | CH₃ | CH₃ |
| 235 | OCH₃ | C(O)H | H | H | CH₃ | CH₃ | CH₃ | CH₃ |
| 236 | OCH₃ | C(O)H | H | H | CH₃ | CH₃ | CH₂CH₃ | CH₃ |
| 237 | OCH₃ | C(O)H | H | H | CH₃ | CH₂CH₃ | CH₃ | CH₃ |
| 238 | OCH₃ | C(O)H | H | CH₃ | CH₃ | H | CH₃ | CH₃ |
| 239 | OCH₃ | C(O)H | H | CH₃ | CH₃ | H | CH₂CH₃ | CH₃ |
| 240 | OCH₃ | C(O)H | H | CH₃ | CH₃ | CH₃ | CH₃ | H |
| 241 | OCH₃ | C(O)H | H | CH₃ | CH₃ | CH₃ | CH₂CH₃ | H |
| 242 | OCH₃ | C(O)H | H | CH₃ | CH₃ | CH₂CH₃ | CH₃ | H |
| 243 | OCH₃ | C(O)H | H | CH₂CH₃ | H | CH₃ | CH₃ | CH₃ |
| 244 | OCH₃ | C(O)H | H | CH₂CH₃ | CH₃ | H | CH₃ | CH₃ |
| 245 | OCH₃ | C(O)H | H | CH₂CH₃ | CH₃ | CH₃ | CH₃ | H |
| 246 | OCH₃ | C(O)H | H | CH(CH₃)₂ | H | CH₃ | CH₃ | CH₃ |
| 247 | OCH₃ | C(O)H | H | CH(CH₃)₂ | CH₃ | H | CH₃ | CH₃ |
| 248 | OCH₃ | C(O)H | CH₃ | H | CH₃ | CH₃ | CH₃ | CH₃ |
| 249 | OCH₃ | C(O)H | CH₃ | H | CH₃ | CH₃ | CH₂CH₃ | CH₃ |
| 250 | OCH₃ | C(O)H | CH₃ | H | CH₃ | CH₂CH₃ | CH₃ | CH₃ |
| 251 | OCH₃ | C(O)H | CH₃ | CH₃ | CH₃ | H | CH₃ | CH₃ |
| 252 | OCH₃ | C(O)H | CH₃ | CH₃ | CH₃ | H | CH₂CH₃ | CH₃ |
| 253 | OCH₃ | C(O)H | CH₃ | CH₃ | CH₃ | CH₃ | CH₃ | H |
| 254 | OCH₃ | C(O)H | CH₃ | CH₃ | CH₃ | CH₃ | CH₂CH₃ | H |
| 255 | OCH₃ | C(O)H | CH₃ | CH₃ | CH₃ | CH₂CH₃ | CH₃ | H |
| 256 | OCH₃ | C(O)H | CH₃ | CH₂CH₃ | H | CH₃ | CH₃ | CH₃ |
| 257 | OCH₃ | C(O)H | CH₃ | CH₂CH₃ | CH₃ | H | CH₃ | CH₃ |
| 258 | OCH₃ | C(O)H | CH₃ | CH₂CH₃ | CH₃ | CH₃ | CH₃ | H |
| 259 | OCH₃ | C(O)H | CH₃ | CH(CH₃)₂ | H | CH₃ | CH₃ | CH₃ |
| 260 | OCH₃ | C(O)H | CH₃ | CH(CH₃)₂ | CH₃ | H | CH₃ | CH₃ |
| 261 | OCH₃ | C(O)H | CH₂CH₃ | H | CH₃ | CH₃ | CH₃ | CH₃ |
| 262 | OCH₃ | C(O)H | CH₂CH₃ | H | CH₃ | CH₃ | CH₂CH₃ | CH₃ |
| 263 | OCH₃ | C(O)H | CH₂CH₃ | H | CH₃ | CH₂CH₃ | CH₃ | CH₃ |
| 264 | OCH₃ | C(O)H | CH₂CH₃ | CH₃ | CH₃ | H | CH₃ | CH₃ |
| 265 | OCH₃ | C(O)H | CH₂CH₃ | CH₃ | CH₃ | H | CH₂CH₃ | CH₃ |
| 266 | OCH₃ | C(O)H | CH₂CH₃ | CH₃ | CH₃ | CH₃ | CH₃ | H |
| 267 | OCH₃ | C(O)H | CH₂CH₃ | CH₃ | CH₃ | CH₃ | CH₂CH₃ | H |
| 268 | OCH₃ | C(O)H | CH₂CH₃ | CH₃ | CH₃ | CH₂CH₃ | CH₃ | H |
| 269 | OCH₃ | C(O)H | CH₂CH₃ | CH₂CH₃ | H | CH₃ | CH₃ | CH₃ |
| 270 | OCH₃ | C(O)H | CH₂CH₃ | CH₂CH₃ | CH₃ | H | CH₃ | CH₃ |
| 271 | OCH₃ | C(O)H | CH₂CH₃ | CH₂CH₃ | CH₃ | CH₃ | CH₃ | H |
| 272 | OCH₃ | C(O)H | CH₂CH₃ | CH(CH₃)₂ | H | CH₃ | CH₃ | CH₃ |
| 273 | OCH₃ | C(O)H | CH₂CH₃ | CH(CH₃)₂ | CH₃ | H | CH₃ | CH₃ |
| 274 | OH | H | C(O)H | H | CH₃ | CH₃ | CH₃ | CH₃ |
| 275 | OH | H | C(O)H | H | CH₃ | CH₃ | CH₂CH₃ | CH₃ |
| 276 | OH | H | C(O)H | H | CH₃ | CH₂CH₃ | CH₃ | CH₃ |
| 277 | OH | H | C(O)H | CH₃ | CH₃ | H | CH₃ | CH₃ |
| 278 | OH | H | C(O)H | CH₃ | CH₃ | H | CH₂CH₃ | CH₃ |
| 279 | OH | H | C(O)H | CH₃ | CH₃ | CH₃ | CH₃ | H |
| 280 | OH | H | C(O)H | CH₃ | CH₃ | CH₃ | CH₂CH₃ | H |
| 281 | OH | H | C(O)H | CH₃ | CH₃ | CH₂CH₃ | CH₃ | H |
| 282 | OH | H | C(O)H | CH₂CH₃ | H | CH₃ | CH₃ | CH₃ |
| 283 | OH | H | C(O)H | CH₂CH₃ | CH₃ | H | CH₃ | CH₃ |
| 284 | OH | H | C(O)H | CH₂CH₃ | CH₃ | CH₃ | CH₃ | H |
| 285 | OH | H | C(O)H | CH(CH₃) | H | CH₃ | CH₃ | CH₃ |
| 286 | OH | H | C(O)H | CH(CH₃)₂ | CH₃ | H | CH₃ | CH₃ |
| 287 | OH | CH₃ | C(O)H | H | CH₃ | CH₃ | CH₃ | CH₃ |
| 288 | OH | CH₃ | C(O)H | H | CH₃ | CH₃ | CH₂CH₃ | CH₃ |
| 289 | OH | CH₃ | C(O)H | H | CH₃ | CH₂CH₃ | CH₃ | CH₃ |
| 290 | OH | CH₃ | C(O)H | CH₃ | CH₃ | H | CH₃ | CH₃ |
| 291 | OH | CH₃ | C(O)H | CH₃ | CH₃ | H | CH₂CH₃ | CH₃ |
| 292 | OH | CH₃ | C(O)H | CH₃ | CH₃ | CH₃ | CH₃ | H |
| 293 | OH | CH₃ | C(O)H | CH₃ | CH₃ | CH₃ | CH₂CH₃ | H |
| 294 | OH | CH₃ | C(O)H | CH₃ | CH₃ | CH₂CH₃ | CH₃ | H |

TABLE I-continued

| Compound | R¹ | R² | R³ | R⁴ | R⁵ | R⁶ | R⁷ | R⁸ |
|---|---|---|---|---|---|---|---|---|
| 295 | OH | CH₃ | C(O)H | CH₂CH₃ | H | CH₃ | CH₃ | CH₃ |
| 296 | OH | CH₃ | C(O)H | CH₂CH₃ | CH₃ | H | CH₃ | CH₃ |
| 297 | OH | CH₃ | C(O)H | CH₂CH₃ | CH₃ | CH₃ | CH₃ | H |
| 298 | OH | CH₃ | C(O)H | CH(CH₃)₂ | H | CH₃ | CH₃ | CH₃ |
| 299 | OH | CH₃ | C(O)H | CH(CH₃)₂ | CH₃ | H | CH₃ | CH₃ |
| 300 | OH | CH₂CH₃ | C(O)H | H | CH₃ | CH₃ | CH₃ | CH₃ |
| 301 | OH | CH₂CH₃ | C(O)H | H | CH₃ | CH₃ | CH₂CH₃ | CH₃ |
| 302 | OH | CH₂CH₃ | C(O)H | H | CH₃ | CH₂CH₃ | CH₃ | CH₃ |
| 303 | OH | CH₂CH₃ | C(O)H | CH₃ | CH₃ | H | CH₃ | CH₃ |
| 304 | OH | CH₂CH₃ | C(O)H | CH₃ | CH₃ | H | CH₂CH₃ | CH₃ |
| 305 | OH | CH₂CH₃ | C(O)H | CH₃ | CH₃ | CH₃ | CH₃ | H |
| 306 | OH | CH₂CH₃ | C(O)H | CH₃ | CH₃ | CH₃ | CH₂CH₃ | H |
| 307 | OH | CH₂CH₃ | C(O)H | CH₃ | CH₃ | CH₂CH₃ | CH₃ | H |
| 308 | OH | CH₂CH₃ | C(O)H | CH₂CH₃ | H | CH₃ | CH₃ | CH₃ |
| 309 | OH | CH₂CH₃ | C(O)H | CH₂CH₃ | CH₃ | H | CH₃ | CH₃ |
| 310 | OH | CH₂CH₃ | C(O)H | CH₂CH₃ | CH₃ | CH₃ | CH₃ | H |
| 311 | OH | CH₂CH₃ | C(O)H | CH(CH₃)₂ | H | CH₃ | CH₃ | CH₃ |
| 312 | OH | CH₂CH₃ | C(O)H | CH(CH₃)₂ | CH₃ | H | CH₃ | CH₃ |
| 313 | OH | C(O)H | H | H | CH₃ | CH₃ | CH₃ | CH₃ |
| 314 | OH | C(O)H | H | H | CH₃ | CH₃ | CH₂CH₃ | CH₃ |
| 315 | OH | C(O)H | H | H | CH₃ | CH₂CH₃ | CH₃ | CH₃ |
| 316 | OH | C(O)H | H | CH₃ | CH₃ | H | CH₃ | CH₃ |
| 317 | OH | C(O)H | H | CH₃ | CH₃ | H | CH₂CH₃ | CH₃ |
| 318 | OH | C(O)H | H | CH₃ | CH₃ | CH₃ | CH₃ | H |
| 319 | OH | C(O)H | H | CH₃ | CH₃ | CH₃ | CH₂CH₃ | H |
| 320 | OH | C(O)H | H | CH₃ | CH₃ | CH₂CH₃ | CH₃ | H |
| 321 | OH | C(O)H | H | CH₂CH₃ | H | CH₃ | CH₃ | CH₃ |
| 322 | OH | C(O)H | H | CH₂CH₃ | CH₃ | H | CH₃ | CH₃ |
| 323 | OH | C(O)H | H | CH₂CH₃ | CH₃ | CH₃ | CH₃ | H |
| 324 | OH | C(O)H | H | CH(CH₃)₂ | H | CH₃ | CH₃ | CH₃ |
| 325 | OH | C(O)H | H | CH(CH₃)₂ | CH₃ | H | CH₃ | CH₃ |
| 326 | OH | C(O)H | CH₃ | H | CH₃ | CH₃ | CH₃ | CH₃ |
| 327 | OH | C(O)H | CH₃ | H | CH₃ | CH₃ | CH₂CH₃ | CH₃ |
| 328 | OH | C(O)H | CH₃ | H | CH₃ | CH₂CH₃ | CH₃ | CH₃ |
| 329 | OH | C(O)H | CH₃ | CH₃ | CH₃ | H | CH₃ | CH₃ |
| 330 | OH | C(O)H | CH₃ | CH₃ | CH₃ | H | CH₂CH₃ | CH₃ |
| 331 | OH | C(O)H | CH₃ | CH₃ | CH₃ | CH₃ | CH₃ | H |
| 332 | OH | C(O)H | CH₃ | CH₃ | CH₃ | CH₃ | CH₂CH₃ | H |
| 333 | OH | C(O)H | CH₃ | CH₃ | CH₃ | CH₂CH₃ | CH₃ | H |
| 334 | OH | C(O)H | CH₃ | CH₂CH₃ | H | CH₃ | CH₃ | CH₃ |
| 335 | OH | C(O)H | CH₃ | CH₂CH₃ | CH₃ | H | CH₃ | CH₃ |
| 336 | OH | C(O)H | CH₃ | CH₂CH₃ | CH₃ | CH₃ | CH₃ | H |
| 337 | OH | C(O)H | CH₃ | CH(CH₃)₂ | H | CH₃ | CH₃ | CH₃ |
| 338 | OH | C(O)H | CH₃ | CH(CH₃)₂ | CH₃ | H | CH₃ | CH₃ |
| 339 | OH | C(O)H | CH₂CH₃ | H | CH₃ | CH₃ | CH₃ | CH₃ |
| 340 | OH | C(O)H | CH₂CH₃ | H | CH₃ | CH₃ | CH₂CH₃ | CH₃ |
| 341 | OH | C(O)H | CH₂CH₃ | H | CH₃ | CH₂CH₃ | CH₃ | CH₃ |
| 342 | OH | C(O)H | CH₂CH₃ | CH₃ | H | CH₂CH₃ | CH₃ | CH₃ |
| 343 | OH | C(O)H | CH₂CH₃ | CH₃ | CH₃ | H | CH₃ | CH₃ |
| 344 | OH | C(O)H | CH₂CH₃ | CH₃ | CH₃ | H | CH₂CH₃ | CH₃ |
| 345 | OH | C(O)H | CH₂CH₃ | CH₃ | CH₃ | CH₃ | CH₃ | H |
| 346 | OH | C(O)H | CH₂CH₃ | CH₃ | CH₃ | CH₃ | CH₂CH₃ | H |
| 347 | OH | C(O)H | CH₂CH₃ | CH₃ | CH₃ | CH₂CH₃ | CH₃ | H |
| 348 | OH | C(O)H | CH₂CH₃ | CH₂CH₃ | H | CH₃ | CH₃ | CH₃ |
| 349 | OH | C(O)H | CH₂CH₃ | CH₂CH₃ | CH₃ | H | CH₃ | CH₃ |
| 350 | OH | C(O)H | CH₂CH₃ | CH₂CH₃ | CH₃ | CH₃ | CH₃ | H |
| 351 | OH | C(O)H | CH₂CH₃ | CH(CH₃)₂ | H | CH₃ | CH₃ | CH₃ |
| 352 | OH | C(O)H | CH₂CH₃ | CH(CH₃)₂ | CH₃ | H | CH₃ | CH₃ |
| 353 | CH₃ | OCH₃ | C(O)H | H | CH₃ | CH₃ | CH₃ | CH₃ |
| 354 | CH₃ | OCH₃ | C(O)H | H | CH₃ | CH₂CH₃ | CH₃ | CH₃ |
| 355 | CH₃ | OCH₃ | C(O)H | H | CH₃ | CH₃ | CH₂CH₃ | CH₃ |
| 356 | CH₃ | OCH₃ | C(O)H | CH₃ | CH₃ | H | CH₃ | CH₃ |
| 357 | CH₃ | OCH₃ | C(O)H | CH₃ | CH₃ | H | CH₂CH₃ | CH₃ |
| 358 | CH₃ | OCH₃ | C(O)H | CH₃ | CH₃ | CH₃ | CH₃ | H |
| 359 | CH₃ | OCH₃ | C(O)H | CH₃ | CH₃ | CH₃ | CH₂CH₃ | H |
| 360 | CH₃ | OCH₃ | C(O)H | CH₃ | CH₃ | CH₂CH₃ | CH₃ | H |
| 361 | CH₃ | OCH₃ | C(O)H | CH₂CH₃ | H | CH₃ | CH₃ | CH₃ |
| 362 | CH₃ | OCH₃ | C(O)H | CH₂CH₃ | CH₃ | H | CH₃ | CH₃ |
| 363 | CH₃ | OCH₃ | C(O)H | CH₂CH₃ | CH₃ | CH₃ | CH₃ | H |
| 364 | CH₃ | OCH₃ | C(O)H | CH₂CH₃ | CH₃ | CH₃ | CH₃ | CH₃ |
| 365 | CH₃ | OCH₃ | C(O)H | CH(CH₃)₂ | H | CH₃ | CH₃ | CH₃ |
| 366 | CH₃ | OCH₃ | C(O)H | CH(CH₃)₂ | CH₃ | H | CH₃ | CH₃ |
| 367 | CH₃ | OH | C(O)H | H | CH₃ | CH₃ | CH₃ | CH₃ |
| 368 | CH₃ | OH | C(O)H | H | CH₃ | CH₂CH₃ | CH₃ | CH₃ |
| 369 | CH₃ | OH | C(O)H | H | CH₃ | CH₃ | CH₂CH₃ | CH₃ |
| 370 | CH₃ | OH | C(O)H | CH₃ | CH₃ | H | CH₃ | CH₃ |
| 371 | CH₃ | OH | C(O)H | CH₃ | CH₃ | H | CH₂CH₃ | CH₃ |
| 372 | CH₃ | OH | C(O)H | CH₃ | CH₃ | CH₃ | CH₃ | H |
| 373 | CH₃ | OH | C(O)H | CH₃ | CH₃ | CH₃ | CH₂CH₃ | H |
| 374 | CH₃ | OH | C(O)H | CH₃ | CH₃ | CH₂CH₃ | CH₃ | H |
| 375 | CH₃ | OH | C(O)H | CH₂CH₃ | H | CH₃ | CH₃ | CH₃ |

TABLE I-continued

| Compound | R¹ | R² | R³ | R⁴ | R⁵ | R⁶ | R⁷ | R⁸ |
|---|---|---|---|---|---|---|---|---|
| 376 | CH₃ | OH | C(O)H | CH₂CH₃ | CH₃ | H | CH₃ | H |
| 377 | CH₃ | OH | C(O)H | CH₂CH₃ | CH₃ | CH₃ | CH₃ | H |
| 378 | CH₃ | OH | C(O)H | CH₂CH₃ | CH₃ | CH₃ | CH₃ | CH₃ |
| 379 | CH₃ | OH | C(O)H | CH(CH₃)₂ | H | CH₃ | CH₃ | CH₃ |
| 380 | CH₃ | OH | C(O)H | CH(CH₃)₂ | CH₃ | H | CH₃ | CH₃ |
| 381 | CH₃ | C(O)H | OCH₃ | H | CH₃ | CH₃ | CH₃ | CH₃ |
| 382 | CH₃ | C(O)H | OCH₃ | H | CH₃ | CH₂CH₃ | CH₃ | CH₃ |
| 383 | CH₃ | C(O)H | OCH₃ | H | CH₃ | CH₃ | CH₂CH₃ | CH₃ |
| 384 | CH₃ | C(O)H | OCH₃ | CH₃ | CH₃ | H | CH₃ | CH₃ |
| 385 | CH₃ | C(O)H | OCH₃ | CH₃ | CH₃ | H | CH₂CH₃ | CH₃ |
| 386 | CH₃ | C(O)H | OCH₃ | CH₃ | CH₃ | CH₃ | CH₃ | H |
| 387 | CH₃ | C(O)H | OCH₃ | CH₃ | CH₃ | CH₃ | CH₂CH₃ | H |
| 388 | CH₃ | C(O)H | OCH₃ | CH₃ | CH₃ | CH₂CH₃ | CH₃ | H |
| 389 | CH₃ | C(O)H | OCH₃ | CH₂CH₃ | H | CH₃ | CH₃ | CH₃ |
| 390 | CH₃ | C(O)H | OCH₃ | CH₂CH₃ | CH₃ | H | CH₃ | CH₃ |
| 391 | CH₃ | C(O)H | OCH₃ | CH₂CH₃ | CH₃ | CH₃ | CH₃ | H |
| 392 | CH₃ | C(O)H | OCH₃ | CH₂CH₃ | CH₃ | CH₃ | CH₃ | CH₃ |
| 393 | CH₃ | C(O)H | OCH₃ | CH(CH₃)₂ | H | CH₃ | CH₃ | CH₃ |
| 394 | CH₃ | C(O)H | OCH₃ | CH(CH₃)₂ | CH₃ | H | CH₃ | CH₃ |
| 395 | CH₃ | C(O)H | OH | H | CH₃ | CH₃ | CH₃ | CH₃ |
| 396 | CH₃ | C(O)H | OH | H | CH₃ | CH₂CH₃ | CH₃ | CH₃ |
| 397 | CH₃ | C(O)H | OH | H | CH₃ | CH₃ | CH₂CH₃ | CH₃ |
| 398 | CH₃ | C(O)H | OH | CH₃ | CH₃ | H | CH₃ | CH₃ |
| 399 | CH₃ | C(O)H | OH | CH₃ | CH₃ | H | CH₂CH₃ | CH₃ |
| 400 | CH₃ | C(O)H | OH | CH₃ | CH₃ | CH₃ | CH₃ | H |
| 401 | CH₃ | C(O)H | OH | CH₃ | CH₃ | CH₃ | CH₂CH₃ | H |
| 402 | CH₃ | C(O)H | OH | CH₃ | CH₃ | CH₂CH₃ | CH₃ | H |
| 403 | CH₃ | C(O)H | OH | CH₂CH₃ | H | CH₃ | CH₃ | CH₃ |
| 404 | CH₃ | C(O)H | OH | CH₂CH₃ | CH₃ | H | CH₃ | CH₃ |
| 405 | CH₃ | C(O)H | OH | CH₂CH₃ | CH₃ | CH₃ | CH₃ | H |
| 406 | CH₃ | C(O)H | OH | CH₂CH₃ | CH₃ | CH₃ | CH₃ | CH₃ |
| 407 | CH₃ | C(O)H | OH | CH(CH₃)₂ | H | CH₃ | CH₃ | CH₃ |
| 408 | CH₃ | C(O)H | OH | CH(CH₃)₂ | CH₃ | H | CH₃ | CH₃ |
| 409 | CH₂CH₃ | OCH₃ | C(O)H | H | CH₃ | CH₃ | CH₃ | CH₃ |
| 410 | CH₂CH₃ | OCH₃ | C(O)H | H | CH₃ | CH₂CH₃ | CH₃ | CH₃ |
| 411 | CH₂CH₃ | OCH₃ | C(O)H | H | CH₃ | CH₃ | CH₂CH₃ | CH₃ |
| 412 | CH₂CH₃ | OCH₃ | C(O)H | CH₃ | CH₃ | H | CH₃ | CH₃ |
| 413 | CH₂CH₃ | OCH₃ | C(O)H | CH₃ | CH₃ | H | CH₂CH₃ | CH₃ |
| 414 | CH₂CH₃ | OCH₃ | C(O)H | CH₃ | CH₃ | CH₃ | CH₃ | H |
| 415 | CH₂CH₃ | OCH₃ | C(O)H | CH₃ | CH₃ | CH₃ | CH₂CH₃ | H |
| 416 | CH₂CH₃ | OCH₃ | C(O)H | CH₃ | CH₃ | CH₂CH₃ | CH₃ | H |
| 417 | CH₂CH₃ | OCH₃ | C(O)H | CH₂CH₃ | H | CH₃ | CH₃ | CH₃ |
| 418 | CH₂CH₃ | OCH₃ | C(O)H | CH₂CH₃ | CH₃ | H | CH₃ | CH₃ |
| 419 | CH₂CH₃ | OCH₃ | C(O)H | CH₂CH₃ | CH₃ | CH₃ | CH₃ | H |
| 420 | CH₂CH₃ | OCH₃ | C(O)H | CH₂CH₃ | CH₃ | CH₃ | CH₃ | CH₃ |
| 421 | CH₂CH₃ | OCH₃ | C(O)H | CH(CH₃)₂ | H | CH₃ | CH₃ | CH₃ |
| 422 | CH₂CH₃ | OCH₃ | C(O)H | CH(CH₃)₂ | CH₃ | H | CH₃ | CH₃ |
| 423 | CH₂CH₃ | OH | C(O)H | H | CH₃ | CH₃ | CH₃ | CH₃ |
| 424 | CH₂CH₃ | OH | C(O)H | H | CH₃ | CH₂CH₃ | CH₃ | CH₃ |
| 425 | CH₂CH₃ | OH | C(O)H | H | CH₃ | CH₃ | CH₂CH₃ | CH₃ |
| 426 | CH₂CH₃ | OH | C(O)H | CH₃ | CH₃ | H | CH₃ | CH₃ |
| 427 | CH₂CH₃ | OH | C(O)H | CH₃ | CH₃ | H | CH₂CH₃ | CH₃ |
| 428 | CH₂CH₃ | OH | C(O)H | CH₃ | CH₃ | CH₃ | CH₃ | H |
| 429 | OH | C(O)H | CH₃ | CH₃ | CH₃ | CH₂CH₃ | H | |
| 430 | CH₂CH₃ | OH | C(O)H | CH₃ | CH₃ | CH₂CH₃ | CH₃ | H |
| 431 | CH₂CH₃ | OH | C(O)H | CH₂CH₃ | H | CH₃ | CH₃ | CH₃ |
| 432 | CH₂CH₃ | OH | C(O)H | CH₂CH₃ | CH₃ | H | CH₃ | CH₃ |
| 433 | CH₂CH₃ | OH | C(O)H | CH₂CH₃ | CH₃ | CH₃ | CH₃ | H |
| 434 | CH₂CH₃ | OH | C(O)H | CH₂CH₃ | CH₃ | CH₃ | CH₃ | CH₃ |
| 435 | CH₂CH₃ | OH | C(O)H | CH(CH₃)₂ | H | CH₃ | CH₃ | CH₃ |
| 436 | CH₂CH₃ | OH | C(O)H | CH(CH₃)₂ | CH₃ | H | CH₃ | CH₃ |
| 437 | CH₂CH₃ | C(O)H | OCH₃ | H | CH₃ | CH₃ | CH₃ | CH₃ |
| 438 | CH₂CH₃ | C(O)H | OCH₃ | H | CH₃ | CH₂CH₃ | CH₃ | CH₃ |
| 439 | CH₂CH₃ | C(O)H | OCH₃ | H | CH₃ | CH₃ | CH₂CH₃ | CH₃ |
| 440 | CH₂CH₃ | C(O)H | OCH₃ | CH₃ | CH₃ | H | CH₃ | CH₃ |
| 441 | CH₂CH₃ | C(O)H | OCH₃ | CH₃ | CH₃ | H | CH₂CH₃ | CH₃ |
| 442 | CH₂CH₃ | C(O)H | OCH₃ | CH₃ | CH₃ | CH₃ | CH₃ | H |
| 443 | CH₂CH₃ | C(O)H | OCH₃ | CH₃ | CH₃ | CH₃ | CH₂CH₃ | H |
| 444 | CH₂CH₃ | C(O)H | OCH₃ | CH₃ | CH₃ | CH₂CH₃ | CH₃ | H |
| 445 | CH₂CH₃ | C(O)H | OCH₃ | CH₂CH₃ | H | CH₃ | CH₃ | CH₃ |
| 446 | CH₂CH₃ | C(O)H | OCH₃ | CH₂CH₃ | CH₃ | H | CH₃ | CH₃ |
| 447 | CH₂CH₃ | C(O)H | OCH₃ | CH₂CH₃ | CH₃ | CH₃ | CH₃ | H |
| 448 | CH₂CH₃ | C(O)H | OCH₃ | CH₂CH₃ | CH₃ | CH₃ | CH₃ | CH₃ |
| 449 | CH₂CH₃ | C(O)H | OCH₃ | CH(CH₃)₂ | H | CH₃ | CH₃ | CH₃ |
| 450 | CH₂CH₃ | C(O)H | OCH₃ | CH(CH₃)₂ | CH₃ | H | CH₃ | CH₃ |
| 451 | CH₂CH₃ | C(O)H | OH | H | CH₃ | CH₃ | CH₃ | CH₃ |
| 452 | CH₂CH₃ | C(O)H | OH | H | CH₃ | CH₂CH₃ | CH₃ | CH₃ |
| 453 | CH₂CH₃ | C(O)H | OH | H | CH₃ | CH₃ | CH₂CH₃ | CH₃ |
| 454 | CH₂CH₃ | C(O)H | OH | CH₃ | CH₃ | H | CH₃ | CH₃ |
| 455 | CH₂CH₃ | C(O)H | OH | CH₃ | CH₃ | H | CH₂CH₃ | CH₃ |
| 456 | CH₂CH₃ | C(O)H | OH | CH₃ | CH₃ | CH₃ | CH₃ | H |

TABLE I-continued

| Compound | R¹ | R² | R³ | R⁴ | R⁵ | R⁶ | R⁷ | R⁸ |
|---|---|---|---|---|---|---|---|---|
| 457 | $CH_2CH_3$ | $C(O)H$ | $OH$ | $CH_3$ | $CH_3$ | $CH_3$ | $CH_2CH_3$ | H |
| 458 | $CH_2CH_3$ | $C(O)H$ | $OH$ | $CH_3$ | $CH_3$ | $CH_2CH_3$ | $CH_3$ | H |
| 459 | $CH_2CH_3$ | $C(O)H$ | $OH$ | $CH_2CH_3$ | H | $CH_3$ | $CH_3$ | $CH_3$ |
| 460 | $CH_2CH_3$ | $C(O)H$ | $OH$ | $CH_2CH_3$ | $CH_3$ | H | $CH_3$ | $CH_3$ |
| 461 | $CH_2CH_3$ | $C(O)H$ | $OH$ | $CH_2CH_3$ | $CH_3$ | $CH_3$ | $CH_3$ | H |
| 462 | $CH_2CH_3$ | $C(O)H$ | $OH$ | $CH_2CH_3$ | $CH_3$ | $CH_3$ | $CH_3$ | $CH_3$ |
| 463 | $CH_2CH_3$ | $C(O)H$ | $OH$ | $CH(CH_3)_2$ | H | $CH_3$ | $CH_3$ | $CH_3$ |
| 464 | $CH_2CH_3$ | $C(O)H$ | $OH$ | $CH(CH_3)_2$ | $CH_3$ | H | $CH_3$ | $CH_3$ |
| 465 | $OCH_3$ | $OCH_3$ | $C(O)H$ | H | $CH_3$ | $CH_3$ | $CH_3$ | $CH_3$ |
| 466 | $OCH_3$ | $OCH_3$ | $C(O)H$ | H | $CH_3$ | $CH_2CH_3$ | $CH_3$ | $CH_3$ |
| 467 | $OCH_3$ | $OCH_3$ | $C(O)H$ | H | $CH_3$ | $CH_3$ | $CH_2CH_3$ | $CH_3$ |
| 468 | $OCH_3$ | $OCH_3$ | $C(O)H$ | $CH_3$ | $CH_3$ | H | $CH_3$ | $CH_3$ |
| 469 | $OCH_3$ | $OCH_3$ | $C(O)H$ | $CH_3$ | $CH_3$ | H | $CH_2CH_3$ | $CH_3$ |
| 470 | $OCH_3$ | $OCH_3$ | $C(O)H$ | $CH_3$ | $CH_3$ | $CH_3$ | $CH_3$ | H |
| 471 | $OCH_3$ | $OCH_3$ | $C(O)H$ | $CH_3$ | $CH_3$ | $CH_3$ | $CH_2CH_3$ | H |
| 472 | $OCH_3$ | $OCH_3$ | $C(O)H$ | $CH_3$ | $CH_3$ | $CH_2CH_3$ | $CH_3$ | H |
| 473 | $OCH_3$ | $OCH_3$ | $C(O)H$ | $CH_2CH_3$ | H | $CH_3$ | $CH_3$ | $CH_3$ |
| 474 | $OCH_3$ | $OCH_3$ | $C(O)H$ | $CH_2CH_3$ | $CH_3$ | H | $CH_3$ | $CH_3$ |
| 475 | $OCH_3$ | $OCH_3$ | $C(O)H$ | $CH_2CH_3$ | $CH_3$ | $CH_3$ | $CH_3$ | H |
| 476 | $OCH_3$ | $OCH_3$ | $C(O)H$ | $CH_2CH_3$ | $CH_3$ | $CH_3$ | $CH_3$ | $CH_3$ |
| 477 | $OCH_3$ | $OCH_3$ | $C(O)H$ | $CH(CH_3)_2$ | H | $CH_3$ | $CH_3$ | $CH_3$ |
| 478 | $OCH_3$ | $OCH_3$ | $C(O)H$ | $CH(CH_3)_2$ | $CH_3$ | H | $CH_3$ | $CH_3$ |
| 479 | $OCH_3$ | $C(O)H$ | $OCH_3$ | H | $CH_3$ | $CH_3$ | $CH_3$ | $CH_3$ |
| 480 | $OCH_3$ | $C(O)H$ | $OCH_3$ | H | $CH_3$ | $CH_2CH_3$ | $CH_3$ | $CH_3$ |
| 481 | $OCH_3$ | $C(O)H$ | $OCH_3$ | H | $CH_3$ | $CH_3$ | $CH_2CH_3$ | $CH_3$ |
| 482 | $OCH_3$ | $C(O)H$ | $OCH_3$ | $CH_3$ | $CH_3$ | H | $CH_3$ | $CH_3$ |
| 483 | $OCH_3$ | $C(O)H$ | $OCH_3$ | $CH_3$ | $CH_3$ | H | $CH_2CH_3$ | $CH_3$ |
| 484 | $OCH_3$ | $C(O)H$ | $OCH_3$ | $CH_3$ | $CH_3$ | $CH_3$ | $CH_3$ | H |
| 485 | $OCH_3$ | $C(O)H$ | $OCH_3$ | $CH_3$ | $CH_3$ | $CH_3$ | $CH_2CH_3$ | H |
| 486 | $OCH_3$ | $C(O)H$ | $OCH_3$ | $CH_3$ | $CH_3$ | $CH_2CH_3$ | $CH_3$ | H |
| 487 | $OCH_3$ | $OC(O)H$ | $OCH_3$ | $CH_2CH_3$ | H | $CH_3$ | $CH_3$ | $CH_3$ |
| 488 | $OCH_3$ | $C(O)H$ | $OCH_3$ | $CH_2CH_3$ | $CH_3$ | H | $CH_3$ | $CH_3$ |
| 489 | $OCH_3$ | $C(O)H$ | $OCH_3$ | $CH_2CH_3$ | $CH_3$ | $CH_3$ | $CH_3$ | H |
| 490 | $OCH_3$ | $C(O)H$ | $OCH_3$ | $CH_2CH_3$ | $CH_3$ | $CH_3$ | $CH_3$ | $CH_3$ |
| 491 | $OCH_3$ | $C(O)H$ | $OCH_3$ | $CH(CH_3)_2$ | H | $CH_3$ | $CH_3$ | $CH_3$ |
| 492 | $OCH_3$ | $C(O)H$ | $OCH_3$ | $CH(CH_3)_2$ | $CH_3$ | H | $CH_3$ | $CH_3$ |
| 493 | H | H | $C(O)H$ | $CH_3$ | $CH_3$ | $CH_3$ | $CH_3$ | $CH_3$ |
| 494 | H | H | $C(O)H$ | $CH_2CH_3$ | $CH_3$ | $CH_3$ | $CH_3$ | $CH_3$ |
| 495 | H | H | $C(O)H$ | $CH_3$ | $CH_3$ | $CH_2CH_3$ | $CH_3$ | $CH_3$ |
| 496 | H | H | $C(O)H$ | $CH_3$ | $CH_3$ | $CH_3$ | $CH_2CH_3$ | $CH_3$ |
| 497 | H | $CH_3$ | $C(O)H$ | $CH_2CH_3$ | $CH_3$ | $CH_3$ | $CH_3$ | $CH_3$ |
| 498 | H | $CH_3$ | $C(O)H$ | $CH_3$ | $CH_3$ | $CH_2CH_3$ | $CH_3$ | $CH_3$ |
| 499 | H | $CH_2CH_3$ | $C(O)H$ | $CH_3$ | $CH_3$ | $CH_3$ | $CH_3$ | $CH_3$ |
| 500 | H | $CH_2CH_3$ | $C(O)H$ | $CH_2CH_3$ | $CH_3$ | $CH_3$ | $CH_3$ | $CH_3$ |
| 501 | H | $CH_2CH_3$ | $C(O)H$ | $CH_3$ | $CH_3$ | $CH_2CH_3$ | $CH_3$ | $CH_3$ |
| 502 | H | $CH_2CH_3$ | $C(O)H$ | $CH_3$ | $CH_3$ | $CH_3$ | $CH_2CH_3$ | $CH_3$ |
| 503 | $CH_3$ | H | $C(O)H$ | $CH_3$ | $CH_3$ | $CH_3$ | $CH_3$ | $CH_3$ |
| 504 | $CH_3$ | H | $C(O)H$ | $CH_2CH_3$ | $CH_3$ | $CH_3$ | $CH_3$ | $CH_3$ |
| 505 | $CH_3$ | H | $C(O)H$ | $CH_3$ | $CH_3$ | $CH_2CH_3$ | $CH_3$ | $CH_3$ |
| 506 | $CH_3$ | H | $C(O)H$ | $CH_3$ | $CH_3$ | $CH_3$ | $CH_2CH_3$ | $CH_3$ |
| 507 | $CH_3$ | $CH_3$ | $C(O)H$ | $CH_3$ | $CH_3$ | $CH_3$ | $CH_3$ | $CH_3$ |
| 508 | $CH_3$ | $CH_3$ | $C(O)H$ | $CH_2CH_3$ | $CH_3$ | $CH_3$ | $CH_3$ | $CH_3$ |
| 509 | $CH_3$ | $CH_3$ | $C(O)H$ | $CH_3$ | $CH_3$ | $CH_2CH_3$ | $CH_3$ | $CH_3$ |
| 510 | $CH_3$ | $CH_3$ | $C(O)H$ | $CH_3$ | $CH_3$ | $CH_3$ | $CH_2CH_3$ | $CH_3$ |
| 511 | $CH_3$ | $CH_2CH_3$ | $C(O)H$ | $CH_3$ | $CH_3$ | $CH_3$ | $CH_3$ | $CH_3$ |
| 512 | $CH_3$ | $CH_2CH_3$ | $C(O)H$ | $CH_2CH_3$ | $CH_3$ | $CH_3$ | $CH_3$ | $CH_3$ |
| 513 | $CH_3$ | $CH_2CH_3$ | $C(O)H$ | $CH_3$ | $CH_3$ | $CH_2CH_3$ | $CH_3$ | $CH_3$ |
| 514 | $CH_3$ | $CH_2CH_3$ | $C(O)H$ | $CH_3$ | $CH_3$ | $CH_3$ | $CH_2CH_3$ | $CH_3$ |
| 515 | $CH_3$ | $OCH_3$ | $C(O)H$ | $CH_3$ | $CH_3$ | $CH_3$ | $CH_3$ | $CH_3$ |
| 516 | $CH_3$ | $OCH_3$ | $C(O)H$ | $CH_3$ | $CH_3$ | $CH_2CH_3$ | $CH_3$ | $CH_3$ |
| 517 | $CH_3$ | $OCH_3$ | $C(O)H$ | $CH_3$ | $CH_3$ | $CH_3$ | $CH_2CH_3$ | $CH_3$ |
| 518 | $CH_3$ | $OH$ | $C(O)H$ | $CH_3$ | $CH_3$ | $CH_3$ | $CH_3$ | $CH_3$ |
| 519 | $CH_3$ | $OH$ | $C(O)H$ | $CH_3$ | $CH_3$ | $CH_2CH_3$ | $CH_3$ | $CH_3$ |
| 520 | $CH_3$ | $OH$ | $C(O)H$ | $CH_3$ | $CH_3$ | $CH_3$ | $CH_2CH_3$ | $CH_3$ |
| 521 | $CH_2CH_3$ | H | $C(O)H$ | $CH_3$ | $CH_3$ | $CH_3$ | $CH_3$ | $CH_3$ |
| 522 | $CH_2CH_3$ | H | $C(O)H$ | $CH_2CH_3$ | $CH_3$ | $CH_3$ | $CH_3$ | $CH_3$ |
| 523 | $CH_2CH_3$ | H | $C(O)H$ | $CH_3$ | $CH_3$ | $CH_2CH_3$ | $CH_3$ | $CH_3$ |
| 524 | $CH_2CH_3$ | H | $C(O)H$ | $CH_3$ | $CH_3$ | $CH_3$ | $CH_2CH_3$ | $CH_3$ |
| 525 | $CH_2CH_3$ | $CH_3$ | $C(O)H$ | $CH_3$ | $CH_3$ | $CH_3$ | $CH_3$ | $CH_3$ |
| 526 | $CH_2CH_3$ | $CH_3$ | $C(O)H$ | $CH_2CH_3$ | $CH_3$ | $CH_3$ | $CH_3$ | $CH_3$ |
| 527 | $CH_2CH_3$ | $CH_3$ | $C(O)H$ | $CH_3$ | $CH_3$ | $CH_2CH_3$ | $CH_3$ | $CH_3$ |
| 528 | $CH_2CH_3$ | $CH_3$ | $C(O)H$ | $CH_3$ | $CH_3$ | $CH_3$ | $CH_2CH_3$ | $CH_3$ |
| 529 | $CH_2CH_3$ | $CH_2CH_3$ | $C(O)H$ | $CH_3$ | $CH_3$ | $CH_3$ | $CH_3$ | $CH_3$ |
| 530 | $CH_2CH_3$ | $CH_2CH_3$ | $C(O)H$ | $CH_2CH_3$ | $CH_3$ | $CH_3$ | $CH_3$ | $CH_3$ |
| 531 | $CH_2CH_3$ | $CH_2CH_3$ | $C(O)H$ | $CH_3$ | $CH_3$ | $CH_2CH_3$ | $CH_3$ | $CH_3$ |
| 532 | $CH_2CH_3$ | $CH_2CH_3$ | $C(O)H$ | $CH_3$ | $CH_3$ | $CH_3$ | $CH_2CH_3$ | $CH_3$ |
| 533 | $CH_2CH_3$ | $OCH_3$ | $C(O)H$ | $CH_3$ | $CH_3$ | $CH_3$ | $CH_3$ | $CH_3$ |
| 534 | $CH_2CH_3$ | $OCH_3$ | $C(O)H$ | $CH_3$ | $CH_3$ | $CH_2CH_3$ | $CH_3$ | $CH_3$ |
| 535 | $CH_2CH_3$ | $OCH_3$ | $C(O)H$ | $CH_3$ | $CH_3$ | $CH_3$ | $CH_2CH_3$ | $CH_3$ |
| 536 | $CH_2CH_3$ | $OH$ | $C(O)H$ | $CH_3$ | $CH_3$ | $CH_3$ | $CH_3$ | $CH_3$ |
| 537 | $CH_2CH_3$ | $OH$ | $C(O)H$ | $CH_3$ | $CH_3$ | $CH_2CH_3$ | $CH_3$ | $CH_3$ |

TABLE I-continued

| Compound | R¹ | R² | R³ | R⁴ | R⁵ | R⁶ | R⁷ | R⁸ |
|---|---|---|---|---|---|---|---|---|
| 538 | CH₂CH₃ | OH | C(O)H | CH₃ | CH₃ | CH₃ | CH₂CH₃ | CH₃ |
| 539 | OCH₃ | H | C(O)H | CH₃ | CH₃ | CH₃ | CH₃ | CH₃ |
| 540 | OCH₃ | H | C(O)H | CH₂CH₃ | CH₃ | CH₃ | CH₃ | CH₃ |
| 541 | OCH₃ | H | C(O)H | CH₃ | CH₃ | CH₂CH₃ | CH₃ | CH₃ |
| 542 | OCH₃ | H | C(O)H | CH₃ | CH₃ | CH₃ | CH₂CH₃ | CH₃ |
| 543 | OCH₃ | CH₃ | C(O)H | CH₃ | CH₃ | CH₃ | CH₃ | CH₃ |
| 544 | OCH₃ | CH₃ | C(O)H | CH₂CH₃ | CH₃ | CH₃ | CH₃ | CH₃ |
| 545 | OCH₃ | CH₃ | C(O)H | CH₃ | CH₃ | CH₂CH₃ | CH₃ | CH₃ |
| 546 | OCH₃ | CH₃ | C(O)H | CH₃ | CH₃ | CH₃ | CH₂CH₃ | CH₃ |
| 547 | OCH₃ | CH₂CH₃ | C(O)H | CH₃ | CH₃ | CH₃ | CH₃ | CH₃ |
| 548 | OCH₃ | CH₂CH₃ | C(O)H | CH₂CH₃ | CH₃ | CH₃ | CH₃ | CH₃ |
| 549 | OCH₃ | CH₂CH₃ | C(O)H | CH₃ | CH₃ | CH₂CH₃ | CH₃ | CH₃ |
| 550 | OCH₃ | CH₂CH₃ | C(O)H | CH₃ | CH₃ | CH₃ | CH₂CH₃ | CH₃ |
| 551 | OCH₃ | OCH₃ | C(O)H | CH₃ | CH₃ | CH₃ | CH₃ | CH₃ |
| 552 | OCH₃ | OCH₃ | C(O)H | CH₃ | CH₃ | CH₂CH₃ | CH₃ | CH₃ |
| 553 | OCH₃ | OCH₃ | C(O)H | CH₃ | CH₃ | CH₃ | CH₂CH₃ | CH₃ |
| 554 | OH | H | C(O)H | CH₃ | CH₃ | CH₃ | CH₃ | CH₃ |
| 555 | OH | H | C(O)H | CH₂CH₃ | CH₃ | CH₃ | CH₃ | CH₃ |
| 556 | OH | H | C(O)H | CH₃ | CH₃ | CH₂CH₃ | CH₃ | CH₃ |
| 557 | OH | H | C(O)H | CH₃ | CH₃ | CH₃ | CH₂CH₃ | CH₃ |
| 558 | OH | CH₃ | C(O)H | CH₃ | CH₃ | CH₃ | CH₃ | CH₃ |
| 559 | OH | CH₃ | C(O)H | CH₂CH₃ | CH₃ | CH₃ | CH₃ | CH₃ |
| 560 | OH | CH₃ | C(O)H | CH₃ | CH₃ | CH₂CH₃ | CH₃ | CH₃ |
| 561 | OH | CH₃ | C(O)H | CH₃ | CH₃ | CH₃ | CH₂CH₃ | CH₃ |
| 562 | OH | CH₂CH₃ | C(O)H | CH₃ | CH₃ | CH₃ | CH₃ | CH₃ |
| 563 | OH | CH₂CH₃ | C(O)H | CH₂CH₃ | CH₃ | CH₃ | CH₃ | CH₃ |
| 564 | OH | CH₂CH₃ | C(O)H | CH₃ | CH₃ | CH₂CH₃ | CH₃ | CH₃ |
| 565 | OH | CH₂CH₃ | C(O)H | CH₃ | CH₃ | CH₃ | CH₂CH₃ | CH₃ |
| 566 | CH₃ | C(O)H | H | CH₃ | CH₃ | CH₃ | CH₃ | CH₃ |
| 567 | CH₃ | C(O)H | H | CH₂CH₃ | CH₃ | CH₃ | CH₃ | CH₃ |
| 568 | CH₃ | C(O)H | H | CH₃ | CH₃ | CH₂CH₃ | CH₃ | CH₃ |
| 569 | CH₃ | C(O)H | H | CH₃ | CH₃ | CH₃ | CH₂CH₃ | CH₃ |
| 570 | CH₃ | C(O)H | CH₃ | CH₃ | CH₃ | CH₃ | CH₃ | CH₃ |
| 571 | CH₃ | C(O)H | CH₃ | CH₂CH₃ | CH₃ | CH₃ | CH₃ | CH₃ |
| 572 | CH₃ | C(O)H | CH₃ | CH₃ | CH₃ | CH₂CH₃ | CH₃ | CH₃ |
| 573 | CH₃ | C(O)H | CH₃ | CH₃ | CH₃ | CH₃ | CH₂CH₃ | CH₃ |
| 574 | CH₃ | C(O)H | CH₂CH₃ | CH₃ | CH₃ | CH₃ | CH₃ | CH₃ |
| 575 | CH₃ | C(O)H | CH₂CH₃ | CH₂CH₃ | CH₃ | CH₃ | CH₃ | CH₃ |
| 576 | CH₃ | C(O)H | CH₂CH₃ | CH₃ | CH₃ | CH₂CH₃ | CH₃ | CH₃ |
| 577 | CH₃ | C(O)H | CH₂CH₃ | CH₃ | CH₃ | CH₃ | CH₂CH₃ | CH₃ |
| 578 | CH₂CH₃ | C(O)H | H | CH₃ | CH₃ | CH₃ | CH₃ | CH₃ |
| 579 | CH₂CH₃ | C(O)H | H | CH₂CH₃ | CH₃ | CH₃ | CH₃ | CH₃ |
| 580 | CH₂CH₃ | C(O)H | H | CH₃ | CH₃ | CH₂CH₃ | CH₃ | CH₃ |
| 581 | CH₂CH₃ | C(O)H | H | CH₃ | CH₃ | CH₃ | CH₂CH₃ | CH₃ |
| 582 | CH₂CH₃ | C(O)H | CH₃ | CH₃ | CH₃ | CH₃ | CH₃ | CH₃ |
| 583 | CH₂CH₃ | C(O)H | CH₃ | CH₂CH₃ | CH₃ | CH₃ | CH₃ | CH₃ |
| 584 | CH₂CH₃ | C(O)H | CH₃ | CH₃ | CH₃ | CH₂CH₃ | CH₃ | CH₃ |
| 585 | CH₂CH₃ | C(O)H | CH₃ | CH₃ | CH₃ | CH₃ | CH₂CH₃ | CH₃ |
| 586 | CH₂CH₃ | C(O)H | CH₂CH₃ | CH₃ | CH₃ | CH₃ | CH₃ | CH₃ |
| 587 | CH₂CH₃ | C(O)H | CH₂CH₃ | CH₂CH₃ | CH₃ | CH₃ | CH₃ | CH₃ |
| 588 | CH₂CH₃ | C(O)H | CH₂CH₃ | CH₃ | CH₃ | CH₂CH₃ | CH₃ | CH₃ |
| 589 | CH₂CH₃ | C(O)H | CH₂CH₃ | CH₃ | CH₃ | CH₃ | CH₂CH₃ | CH₃ |
| 590 | CH₂CH₃ | C(O)H | OCH₃ | CH₃ | CH₃ | CH₃ | CH₃ | CH₃ |
| 591 | CH₂CH₃ | C(O)H | OCH₃ | CH₃ | CH₃ | CH₂CH₃ | CH₃ | CH₃ |
| 592 | CH₂CH₃ | C(O)H | OCH₃ | CH₃ | CH₃ | CH₃ | CH₂CH₃ | CH₃ |
| 593 | CH₂CH₃ | C(O)H | OH | CH₃ | CH₃ | CH₃ | CH₃ | CH₃ |
| 594 | CH₂CH₃ | C(O)H | OH | CH₃ | CH₃ | CH₂CH₃ | CH₃ | CH₃ |
| 595 | CH₂CH₃ | C(O)H | OH | CH₃ | CH₃ | CH₃ | CH₂CH₃ | CH₃ |
| 596 | OCH₃ | C(O)H | H | CH₃ | CH₃ | CH₃ | CH₃ | CH₃ |
| 597 | OCH₃ | C(O)H | H | CH₂CH₃ | CH₃ | CH₃ | CH₃ | CH₃ |
| 598 | OCH₃ | C(O)H | H | CH₃ | CH₃ | CH₂CH₃ | CH₃ | CH₃ |
| 599 | OCH₃ | C(O)H | H | CH₃ | CH₃ | CH₃ | CH₂CH₃ | CH₃ |
| 600 | OCH₃ | C(O)H | CH₃ | CH₃ | CH₃ | CH₃ | CH₃ | CH₃ |
| 601 | OCH₃ | C(O)H | CH₃ | CH₂CH₃ | CH₃ | CH₃ | CH₃ | CH₃ |
| 602 | OCH₃ | C(O)H | CH₃ | CH₃ | CH₃ | CH₂CH₃ | CH₃ | CH₃ |
| 603 | OCH₃ | C(O)H | CH₃ | CH₃ | CH₃ | CH₃ | CH₂CH₃ | CH₃ |
| 604 | OCH₃ | C(O)H | CH₂CH₃ | CH₃ | CH₃ | CH₃ | CH₃ | CH₃ |
| 605 | OCH₃ | C(O)H | CH₂CH₃ | CH₂CH₃ | CH₃ | CH₃ | CH₃ | CH₃ |
| 606 | OCH₃ | C(O)H | CH₂CH₃ | CH₃ | CH₃ | CH₂CH₃ | CH₃ | CH₃ |
| 607 | OCH₃ | C(O)H | CH₂CH₃ | CH₃ | CH₃ | CH₃ | CH₂CH₃ | CH₃ |
| 608 | OCH₃ | C(O)H | OCH₃ | CH₃ | CH₃ | CH₃ | CH₃ | CH₃ |
| 609 | OCH₃ | C(O)H | OCH₃ | CH₃ | CH₃ | CH₂CH₃ | CH₃ | CH₃ |
| 610 | OCH₃ | C(O)H | OCH₃ | CH₃ | CH₃ | CH₃ | CH₂CH₃ | CH₃ |
| 611 | OH | C(O)H | H | CH₃ | CH₃ | CH₃ | CH₃ | CH₃ |
| 612 | OH | C(O)H | H | CH₂CH₃ | CH₃ | CH₃ | CH₃ | CH₃ |
| 613 | OH | C(O)H | H | CH₃ | CH₃ | CH₂CH₃ | CH₃ | CH₃ |
| 614 | OH | C(O)H | H | CH₃ | CH₃ | CH₃ | CH₂CH₃ | CH₃ |
| 615 | OH | C(O)H | CH₃ | CH₃ | CH₃ | CH₃ | CH₃ | CH₃ |
| 616 | OH | C(O)H | CH₃ | CH₂CH₃ | CH₃ | CH₃ | CH₃ | CH₃ |
| 617 | OH | C(O)H | CH₃ | CH₃ | CH₃ | CH₂CH₃ | CH₃ | CH₃ |
| 618 | OH | C(O)H | CH₃ | CH₃ | CH₃ | CH₃ | CH₂CH₃ | CH₃ |

TABLE I-continued

| Compound | R¹ | R² | R³ | R⁴ | R⁵ | R⁶ | R⁷ | R⁸ |
|---|---|---|---|---|---|---|---|---|
| 619 | OH | C(O)H | CH₃ | CH₃ | CH₃ | CH₃ | CH(CH₃)₂ | CH₃ |
| 620 | OH | C(O)H | CH₂CH₃ | CH₃ | CH₃ | CH₃ | CH₃ | CH₃ |
| 621 | OH | C(O)H | CH₂CH₃ | CH₂CH₃ | CH₃ | CH₃ | CH₃ | CH₃ |
| 622 | OH | C(O)H | CH₂CH₃ | CH₃ | CH₃ | CH₂CH₃ | CH₃ | CH₃ |
| 623 | OH | C(O)H | CH₂CH₃ | CH₃ | CH₃ | CH₃ | CH₂CH₃ | CH₃ |
| 624 | CH₃ | C(O)H | OCH₃ | CH₃ | CH₃ | CH₃ | CH₃ | CH₃ |
| 625 | CH₃ | C(O)H | OCH₃ | CH₃ | CH₃ | CH₂CH₃ | CH₃ | CH₃ |
| 626 | CH₃ | C(O)H | OCH₃ | CH₃ | CH₃ | CH₃ | CH₂CH₃ | CH₃ |
| 627 | CH₃ | C(O)H | OH | CH₃ | CH₃ | CH₃ | CH₃ | CH₃ |
| 628 | CH₃ | C(O)H | OH | CH₃ | CH₃ | CH₂CH₃ | CH₃ | CH₃ |
| 629 | CH₃ | C(O)H | OH | CH₃ | CH₃ | CH₃ | CH₂CH₃ | CH₃ |

The novel alkyl indane aldehyde compounds of the present invention, with their musk aroma properties, have high utility in the fragrance industry. These compounds can be employed alone, in combination with one another, and/or in combination with one or more ingredients to provide excellent musk fragrance compositions. The compounds of the invention are particularly useful in rounding off compositions, and blend particularly well with aldehydes of various fragrance types.

For example, the compounds of Formula [I] may be used as olfactory components in anionic, cationic, nonionic and zwitterionic detergents, soaps, fabric softener compositions, fabric softener articles for use in clothes dryers, space odorants and deodorants, perfumes, colognes, toilet water, toiletries, bath preparations, deodorants, cosmetics, hand lotions, sunscreens, powders, as well as in other ways. The amount of the subject compounds to be used in modifying the olfactory or fragrance properties of a composition (that is, modifying, augmenting, enhancing, or improving the aroma of such compositions), will vary depending upon the particular use intended, as will be readily apparent to those skilled in the art. Although they may be present in major or minor amounts, preferably, because of the strength of their odor, the compounds of the invention are generally employed as a minor ingredient, that is, in an amount of about 0.1 percent by weight of the fragrance composition up to about 50 percent by weight of the fragrance composition, preferably about 0.1 percent by weight up to about 30 percent by weight of the fragrance composition, and most preferably about 0.1 percent by weight up to about 5.0 percent by weight of the fragrance composition. Within these basic parameters, the olfactorily effective amount (that is, the amount of the compounds of Formula [I] effective to modify, augment, enhance or improve the aroma properties of a composition) will be well within the ambit of one skilled in the art, once armed with the present disclosures.

The fragrance compositions of the invention may, if desired, contain a carrier or vehicle (as used herein, the term "carrier" shall be considered synonymous with the term "vehicle"). Such carriers include liquids such as a non-toxic alcohol, a non-toxic glycol, or the like. An example of a non-toxic alcohol is ethyl alcohol. An example of a non-toxic glycol is 1,2-propylene glycol. Alternatively, the carrier can be an absorbent solid such as a gum, e.g., gum arabic, xantham gum or guar gum, or components for encapsulating a composition such as gelatin, by means of coacervation or such as a urea formaldehyde polymer whereby a polymeric shell is formed around a liquid perfume oil center. The amount of the vehicle or carrier will vary depending upon the particular vehicle or carrier employed and use intended, as will be readily apparent to those skilled in the art. However, the vehicle or carrier can generally be employed in an amount of about 5 percent by weight up to about 95 percent by weight of the fragrance composition.

The fragrance composition may alternatively or additionally contain other perfumery materials. Typical additional perfumery materials which may form part of compositions of the invention include: natural essential oils such as lemon oil, mandarin oil, clove leaf oil, petitgrain oil, cedar wood oil, patchouli oil, lavandin oil, neroli oil, ylang oil, rose absolute or jasmine absolute; natural resins such as labdanum resin or olibanum resin; single perfumery chemicals which may be isolated from natural sources or manufactures synthetically, as for example, alcohols such as geraniol, nerol, citronellol, linalol, tetrahydrogeraniol, β-phenylethyl alcohol, methyl phenyl carbinol, dimethyl benzyl carbinol, menthol or cedrol; acetates and other esters derived from such alcohols; aldehydes such as citral, citronellal, hydroxycitronellal, lauric aldehyde, undecylenic aldehyde, cinnamaldehyde, amyl cinnamic aldehyde, vanillin or heliotropin; acetals derived from such aldehydes; ketones such as methyl hexyl ketone, the ionones and the methylionones; phenolic compounds such as eugenol and isoeugenol; other synthetic musks such as musk xylene, musk ketone, hexamethylisochroman, 5-acetylisopropyltetramethylindane, 6-acetyl-hexamethyltetralin (TETRALIDE®, a registered trademark of Bush Boake Allen Limited), 5-acetyl-hexamethylindane and ethylene brassylate; and other materials commonly employed in the art of perfumery. Typically at least five, and usually at least ten, of such materials will be present as components of the active ingredient. The amount of the additional perfumery material will vary depending upon the particular perfumery material employed and use intended, as will be apparent to those skilled in the art.

Fragrance compositions and preparatory techniques are well known in the art, and are disclosed, for example, in "Soap, Perfumery and Cosmetics", by W. A. Poucher, 7th edition, published by Chapman & Hall (London) (1959); "Perfume and Flavour Chemicals", by S. Arctander, published by the author (Montclair) (1959); and "Perfume and Flavour Materials of Natural Origin", also by S. Arctander, self-published (Elizabeth, N.J.) (1960), the disclosures of each of which are incorporated herein by reference, in their entirety.

The invention is further described in the following Examples 1-6, which are prophetic examples illustrating methods of preparation for compounds of the present invention.

Example 1 describes the preparation of 5-formyl-1-isopropyl-2,3,3,4,6-pentamethylindane, a compound of Formula [I] wherein $R_1$ is $CH_3$, $R_2$ is C(O)H, $R_3$ is $CH_3$, $R_4$ is $CH(CH_3)_2$, $R_5$ is H, $R_6$ is $CH_3$, $R_7$ is $CH_3$, and $R_8$ is $CH_3$.

Example 2 describes the preparation of 5-formyl-1-isopropyl-2,3,3,6-tetramethylindane, a compound of Formula [I] wherein $R_1$ is H, $R_2$ is C(O)H, $R_3$ is $CH_3$, $R_4$ is $CH(CH_3)_2$, $R_5$ is H, $R_6$ is $CH_3$, $R_7$ is $CH_3$, and $R_8$ is $CH_3$.

Example 3 describes the preparation of 5-formyl-1-isopropyl-2,3,3,6-tetramethyl-4-methoxyindane, a compound of Formula [I] wherein $R_1$ is $OCH_3$, $R_2$ is C(O)H, $R_3$ is $CH_3$, $R_4$ is $CH(CH_3)_2$, $R_5$ is H, $R_6$ is $CH_3$, $R_7$ is $CH_3$, and $R_8$ is $CH_3$.

Example 4 describes the preparation of 5-formyl-1-isopropyl-2,3,3,4-tetramethyl-6-methoxyindane, a compound of Formula [I] wherein $R_1$ is $CH_3$, $R_2$ is C(O)H, $R_3$ is $OCH_3$, $R_4$ is $CH(CH_3)_2$, $R_5$ is H, $R_6$ is $CH_3$, $R_7$ is $CH_3$, and $R_8$ is $CH_3$.

Example 5 describes the preparation of 5-formyl-1,1,2,3,3,4-hexamethyl-6-methoxyindane, a compound of Formula [I] wherein $R_1$ is $CH_3$, $R_2$ is C(O)H, $R_3$ is $OCH_3$, $R_4$ is $CH_3$, $R_5$ is $CH_3$, $R_6$ is $CH_3$, $R_7$ is $CH_3$, and $R_8$ is $CH_3$.

Example 6 describes the preparation of 5-formyl-1,1,2,3,3,6-hexamethyl-4-methoxyindane, a compound of Formula [I] wherein $R_1$ is $OCH_3$, $R_2$ is C(O)H, $R_3$ is $CH_3$, $R_4$ is $CH_3$, $R_5$ is $CH_3$, $R_6$ is $CH_3$, $R_7$ is $CH_3$, and $R_8$ is $CH_3$.

These examples are intended to be illustrative only, and are not to be construed as limiting the scope of the appended claims.

EXAMPLE 1

Preparation of 5-Formyl-1-Isopropyl-2,3,3,4,6-Pentamethylindane

Isopropylmagnesium chloride (2.0M, 100 ml, 0.2 moles) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added 3,5-dimethylbenzaldehyde (24.46 g) (which may be obtained from Lancaster Synthesis, Inc., Windham, N.H.). After about 2 hours, an aliquot of additional Grignard (20 ml) is added. The solution is then heated at 60° C. for about one hour, and quenched with aqueous $NH_4Cl$. The aqueous layer is then washed several times with methyl tert-butyl ether and rotoevaporated to yield a crude product mixture containing 2-methyl-1-[3',5'-dimethylphenyl]-1-propanol. The product mixture is then fractionated under reduced pressure to further purify the 2-methyl-1-[3',5'-dimethylphenyl-1-propanol compound.

Next, 2-methyl-1-[3',5'-dimethylphenyl-1-propanol is converted to 1-isopropyl-2,3,3,4,6-pentamethylindane by following procedures similar to those described in European Patent Application Publication No. 0 393 742. Specifically, to a stirred solution of 10 ml $TiCl_4$, in 120 ml dichloromethane which has been cooled to −5° C. under nitrogen, is added a mixture of 17.8 g 2-methyl-1-[3',5'-dimethylphenyl-1-propanol, and 14.0 g 2-methyl-2-butene over a two hour period. The reaction mixture is stirred for a further 30 min at −5° C. Thereafter, it is poured into a mixture of 200 ml water and 100 ml concentrated hydrochloric acid and stirred for 15 min. The organic phase is separated and the aqueous phase washed with brine with 50 ml dichloromethane. The combined organic phase is washed twice with 100 ml 10% hydrochloric acid solution, once with 100 ml water, twice with 100 ml 5% sodium carbonate solution, and finally, once again, with water. Solvent is then removed, yielding 1-isopropyl-2,3,3,4,6-pentamethylindane, which is further purified using reduced pressure fractional distillation techniques.

The compound 1-isopropyl-2,3,3,4,6-pentamethylindane is then treated as follows to yield 5-formyl-1-isopropyl-2,3,3,4,6-pentamethylindane. Specifically, 1-isopropyl-2,3,3,5,6-pentamethylindane (12.96 g) is placed in a 1 liter three-necked round bottom flask equipped with a reflux condenser, a stirrer and a dropping funnel. In accordance with the general procedures described in *Organic Syntheses*, Collective Vol. 5, pp. 49–50, by A. Rieche, H. Gross, and E. Hoft, edited by H. E. Baumgarten, John Wiley and Sons (New York, N.Y. 1973), methylene chloride (37.5 ml) is added to the flask. The solution is then cooled in an ice bath, and titanium tetrachloride (19.0 g) is added over a period of about 3 minutes. While the solution is stirred and cooled, α,α-dichloromethyl methyl ether (5.75 g) is added dropwise over a 25 minute period. After the addition is complete, the mixture is stirred for about 5 minutes in the ice bath, for about 30 minutes without cooling, and for about 15 minutes at about 35° C. The reaction mixture is then poured into a separatory funnel containing about 50 g of crushed ice and is shaken thoroughly. The organic layer is separated, and the aqueous solution is extracted with two 10 ml portions of methylene chloride. The combined organic solution is washed three times with 10 ml portions of water. A crystal of hydroquinone is added to the methylene chloride solution, which is then dried over anhydrous sodium sulfate. After evaporation of the solvent, the residue is distilled to yield, as a crude product, 5-formyl-1-isopropyl-2,3,3,4,6-pentamethylindane. The 5-formyl-1-isopropyl-2,3,3,4,6-pentamethylindane is then further purified using standard fractional distillation techniques.

EXAMPLE 2

Preparation of 5-Formyl-1-Isopropyl-2,3,3,6-Tetramethylindane

Isopropylmagnesium chloride (2.0M, 100 ml, 0.2 moles) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added meta-tolualdehyde (24.46 g). After about 2 hours, an aliquot of Grignard (20 ml) is added. The reaction is then heated at 60° C. for about one hour, and quenched with aqueous $NH_4Cl$. The aqueous layer is then washed several times with methyl tert-butyl ether and rotoevaporated to yield a crude product mixture containing 2-methyl-1-[3'-methylphenyl]-1-propanol. The product mixture is then fractionated under reduced pressure further purify 2-methyl-1-[3'-methylphenyl]-1-propanol. The compound 2-methyl-1-[3'-methylphenyl]-1-propanol is then converted to 1-isopropyl-2,3,3,6-tetramethylindane by following the procedures of Example 1.

The compound 1-isopropyl-2,3,3,6-tetramethylindane is then treated as described in Example 1 to yield 5-formyl-1-isopropyl-2,3,3,6-tetramethylindane.

EXAMPLE 3

Preparation of 5-Formyl-1-Isopropyl-2,3,3,6-Tetramethyl-4-Methoxyindane

Isopropylmagnesium chloride (2.0M, 100 ml, 0.2 moles) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added 3-methoxy-5-methyl benzaldehyde (24.46 g), which may be prepared in accordance with the procedures of Syper, *Tetrahedron Letters*, No. 37, pp. 4493–4498 (1966). After about 2 hours, an aliquot of Grignard (20 ml) is added. The solution is then heated at 60° C. for about one hour, and quenched with aqueous NH$_4$Cl. The aqueous layer is then washed several times with methyl tert-butyl ether and rotoevaporated to yield a crude product mixture containing 2-methyl-1-[3'-methoxy-5'-methylphenyl]-1-propanol. The product mixture is then fractionated under reduced pressure to further purify 2-methyl-1-[3'-methoxy-5'-methylphenyl]-1-propanol.

The compound 2-methyl-1-[3'-methoxy-5'-methylphenyl]-1-propanol is then converted to a mixture of 1-isopropyl-2,3,3,6-tetramethyl-4-methoxyindane and 1-isopropyl-2,3,3,4-tetramethyl-6-methoxyindane by following the procedures of Example 1. The mixture of indanes is then subjected to vacuum spinning band distillation techniques to separate out the 1-isopropyl-2,3,3,6-tetramethyl-4-methoxyindane compound.

The 1-isopropyl-2,3,3,6-tetramethyl-4-methoxyindane compound is then treated as described in Example 1 to yield 5-formyl-1-isopropyl-2,3,3,6-tetramethyl-4-methoxyindane.

EXAMPLE 4

Preparation of 6-Formyl-1-Isopropyl-2,3,3,4-Tetramethyl-5-Methoxyindane

The procedures of Example 3 are substantially carried out, except that the compound 1-isopropyl-2,3,3,4-tetramethyl-6-methoxyindane is isolated from the indane mixture using vacuum spinning band distillation techniques for further use.

The compound 1-isopropyl-2,3,3,4-tetramethyl-6-methoxyindane is then treated as described in Example 1 to yield 6-formyl-1-isopropyl-2,3,3,4-tetramethyl-5-methoxyindane.

EXAMPLE 5

Preparation of 5-Formyl-1,1,2,3,3,4-Hexamethyl-6-Methoxyindane

Methylmagnesium bromide (3.0M, 100 ml) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added a mixture of 2,3-dimethyl-4-methoxyacetophenone and 3,4-dimethyl-2-methoxyacetophenone (24.46 g). The mixture of acetophenones may be prepared using the Perrier modification (CH$_3$C(O)Cl, aluminum chloride and methylene chloride) in accordance with the procedures of Perrier, *Chem. Ber.*, Vol. 33, pp. 819 et seq. (1900), and Perrier, *Bull. Soc. Chim. France*, pp. 859 et seq. (1904). After about 2 hours, an aliquot of additional Grignard (20 ml) is added. The solution is then heated at 60° C. for about one hour, and quenched with aqueous NH$_4$Cl. The aqueous layer is then washed several times with methyl tert-butyl ether and rotoevaporated to yield a crude product mixture containing 1-methyl-1-[2'-methoxy-3',4'-dimethylphenyl]-ethanol or 1-methyl-1-[4'-methoxy-2',3'-dimethylphenyl]-ethanol. The product mixture is then subjected to spinning band distillation procedures to separate out the 1-methyl-1-[4'-methoxy-2',3'-dimethylphenyl]-ethanol compound. The compound 1-methyl-1-[4'-methoxy-2',3'-dimethylphenyl]-ethanol is then converted to 1,1,2,3,3,4-hexamethyl-6-methoxyindane by following the procedures of Example 1.

The 1,1,2,3,3,4-hexamethyl-6-methoxyindane (10.8 g) is then heated with copper(II) sulfate pentahydrate (18.04 g) and potassium peroxydisulfate (60.55 g) in acetonitrile and water (1:1, 500 ml) at reflux for about 15 to 20 minutes, following procedures similar to those described in Hauser et al., *Synthesis*, pp. 723–724 (1987). The mixture is then cooled to room temperature and methylene chloride (150 ml) is added. The layers are separated and the aqueous phase is further extracted with additional methylene chloride (2×70 ml). The combined organic solutions are dried with anhydrous sodium sulfate, filtered, and evaporated at reduced pressure to yield 5-formyl-1,1,2,3,3,4-hexamethyl-6-methoxyindane.

EXAMPLE 6

Preparation of 5-Formyl-1,1,2,3,3,6-Hexamethyl-4-Methoxyindane

The procedures of Example 5 are substantially carried out, except that the compound 1-methyl-1-[2'-methoxy-3',4'-dimethylphenyl]-ethanol is isolated from the indane mixture using standard fractional distillation techniques, and used to prepare 1,1,2,3,3,6-hexamethyl-4-methoxyindane.

The compound 1,1,2,3,3,6-hexamethyl-4-methoxyindane is then treated as described in Example 5 to yield 5-formyl-1,1,2,3,3,6-hexamethyl-4-methoxyindane.

The disclosures of each patent and publication cited or described herein are hereby incorporated herein by reference, in their entirety.

Various modifications of the invention, in addition to those shown and described herein, will be readily apparent to those skilled in the art from the foregoing description. Such modifications are also intended to fall within the scope of the appended claims.

What is claimed is:

1. A compound of the formula:

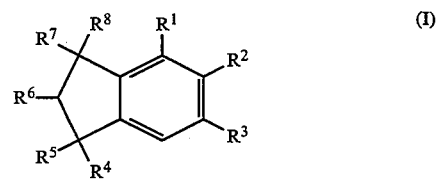

wherein
R$^1$ is H, CH$_3$, CH$_2$CH$_3$, OCH$_3$ or OH,
R$^2$ and R$^3$ are, independently, H, CH$_3$, CH$_2$CH$_3$, OCH$_3$, OH or C(O)H,
R$^4$ and R$^7$ are, independently, H, CH$_3$, CH$_2$CH$_3$ or CH(CH$_3$)$_2$,
R$^5$ and R$^8$ are, independently H or CH$_3$, and
R$^6$ is H, CH$_3$ or CH$_2$CH$_3$, provided that (i) one of $R^2$ and $R^3$ is C(O)H, and one of $R^2$ and $R^3$ is other than C(O)H,
(ii) when $R^1$ is H, then $R^2$ and $R^3$ are other than $OCH_3$ or OH,
(iii) when $R^1$ is other than H, then $R^7$ is $CH_3$ or $CH_2CH_3$,
(iv) no more than one of $R^4$, $R^6$ and $R^7$ is $CH_2CH_3$ or $CH(CH_3)_2$,
(v) no more than one of $R^4$, $R^5$, $R^6$, $R^7$ and $R^8$ is H,
(vi) when each of $R^1$, $R^3$, $R^4$ and $R^5$ are $CH_3$, then $R^8$ is H,
(vii) when $R^4$ is $CH(CH_3)_2$, then at least one of $R^5$ or $R^6$ is H,
(viii) when $R^7$ is $CH(CH_3)_2$, then at least one of $R^6$ or $R^8$ is H,
(ix) when $R^1$ is $OCH_3$, then $R^2$ and $R^3$ are other than OH,
(x) when $R^1$ is OH, then $R^2$ and $R^3$ are other than OH or $OCH_3$,
(xi) when $R^1$ is H, $R^4$ is $CH(CH_3)_2$ and $R^5$ is $CH_3$, then one of $R^2$ and $R^3$ is $CH_2CH_3$,
(xii) when $R^1$ is H, $R^7$ is $CH(CH_3)_2$ and $R^8$ is $CH_3$, then one of $R^2$ and $R^3$ is $CH_2CH_3$,
(xiii) when $R^1$ is H, $R^7$ is $CH(CH_3)_2$ and $R^8$ is H, then $R^3$ is C(O)H,
(xiv) when $R^1$ is H, $R^4$ is $CH(CH_3)_2$ and $R^5$ is H, then $R^2$ is C(O)H,
(xv) when $R^1$ is H, $R^7$ is $CH_2CH_3$ and $R^4$, $R^5$ and $R^8$ is $CH_3$, then both of $R^2$ and $R^3$ are other than $CH_3$,
(xvi) when $R^1$ is H, $R^4$ is $CH_2CH_3$ and $R^5$, $R^7$ and $R^8$ is $CH_3$, then both of $R^2$ and $R^3$ are other than $CH_3$, and
(xvii) when one of $R^2$ and $R^3$ is $CH_3$, and each of $R^4$, $R^5$, $R^6$, $R^7$ and $R^8$ are $CH_3$, then $R^1$ is other than H.

2. A compound of claim 1 wherein $R^2$ is C(O)H.

3. A compound of claim 1 wherein at least one of $R^1$, $R^2$ and $R^3$ are independently $OCH_3$ or OH.

4. A compound of claim 3 wherein at least one of $R^1$, $R^2$ and $R^3$ are $OCH_3$.

5. A compound of claim 1 wherein $R^1$ is H, $CH_3$, $CH_2CH_3$ or $OCH_3$, and $R^2$ and $R^3$ are, independently, H, $CH_3$, $CH_2CH_3$, $OCH_3$ or C(O)H.

6. A compound of claim 5 wherein $R^1$ is H, $CH_3$ or $OCH_3$, and $R^2$ and $R^3$ independently are H, $CH_3$, $OCH_3$ or OC(O)H.

7. A compound of claim 1 wherein at least one of $R^4$ or $R^7$ are H, $CH_3$ or $CH_2CH_3$.

8. A compound of claim 1 wherein $R^4$ and $R^7$ are, independently, $CH_3$, $CH_2CH_3$ or $CH(CH_3)_2$, and $R^5$ and $R^8$ are $CH_3$.

9. A compound of claim 8 wherein $R^6$ is $CH_3$ or $CH_2CH_3$.

10. A compound of claim 1 wherein $R^4$ is $CH(CH_3)_2$.

11. A compound of claim 1 wherein $R^1$ is $CH_3$, $R^2$ is C(O)H, $R^3$ is $OCH_3$, $R^4$ is $CH_3$, $R^5$ is $CH_3$, $R^6$ is $CH_3$, $R^7$ is $CH_3$ and $R^8$ is $CH_3$.

12. A compound of claim 1 wherein $R^1$ is $OCH_3$, $R^2$ is C(O)H, $R^3$ is $CH_3$, $R^4$ is $CH_3$, $R^5$ is $CH_3$, $R^6$ is $CH_3$, $R^7$ is $CH_3$ and $R^8$ is $CH_3$.

13. A compound of claim 1 wherein $R^1$ is $CH_3$, $R^2$ is C(O)H, $R^3$ is $CH_3$, $R^4$ is $CH_2CH_3$, $R^5$ is $CH_3$, $R^6$ is H, $R^7$ is $CH_3$ and $R^8$ is $CH_3$.

14. A compound of claim 1 wherein $R^1$ is $CH_3$, $R^2$ is C(O)H, $R^3$ is $OCH_3$, $R^4$ is $CH_2CH_3$, $R^5$ is $CH_3$, $R^6$ is H, $R^7$ is $CH_3$ and $R^8$ is $CH_3$.

15. A compound of claim 1 wherein $R^1$ is $CH_3$, $R^2$ is C(O)H, $R^3$ is $OCH_3$, $R^4$ is $CH_3$, $R^5$ is $CH_3$, $R^6$ is H, $R^7$ is $CH_2CH_3$ and $R^8$ is $CH_3$.

16. A compound of claim 1 wherein $R^1$ is $OCH_3$, $R^2$ is C(O)H, $R^3$ is $CH_3$, $R^4$ is $CH_2CH_3$, $R^5$ is $CH_3$, $R^6$ is H, $R^7$ is $CH_3$ and $R^8$ is $CH_3$.

17. A compound of claim 1 wherein $R^1$ is $OCH_3$, $R^2$ is C(O)H, $R^3$ is $CH_3$, $R^4$ is $CH_3$, $R^5$ is $CH_3$, $R^6$ is H, $R^7$ is $CH_2CH_3$ and $R^8$ is $CH_3$.

18. A compound of claim 1 wherein $R^1$ is $CH_3$, $R^2$ is C(O)H, $R^3$ is $CH_3$, $R^4$ is $CH(CH_3)_2$, $R^5$ is H, $R^6$ is $CH_3$, $R^7$ is $CH_3$ and $R^8$ is $CH_3$.

19. A compound of claim 1 wherein $R^1$ is $CH_3$, $R^2$ is C(O)H, $R^3$ is $OCH_3$, $R^4$ is $CH(CH_3)_2$, $R^5$ is H, $R^6$ is $CH_3$, $R^7$ is $CH_3$ and $R^8$ is $CH_3$.

20. A compound of claim 1 wherein $R^1$ is $OCH_3$, $R^2$ is C(O)H, $R^3$ is $CH_3$, $R^4$ is $CH(CH_3)_2$, $R^5$ is H, $R^6$ is $CH_3$, $R^7$ is $CH_3$ and $R^8$ is $CH_3$.

21. A compound of claim 1 wherein $R^1$ is $OCH_3$, $R^2$ is C(O)H, $R^3$ is $OCH_3$, $R^4$ is $CH(CH_3)_2$, $R^5$ is H, $R^6$ is $CH_3$, $R^7$ is $CH_3$ and $R^8$ is $CH_3$.

22. A compound of claim 1 wherein $R^1$ is H, $R^2$ is C(O)H, $R^3$ is $CH_3$, $R^4$ is $CH(CH_3)_2$, $R^5$ is H, $R^6$ is $CH_3$, $R^7$ is $CH_3$ and $R^8$ is $CH_3$.

23. A fragrance composition comprising a compound of claim 1 in combination with at least one of a carrier and additional perfumery material.

24. A fragrance composition comprising a compound of claim 21 in combination with at least one of a carrier and additional perfumery material.

25. A method of modifying the olfactory properties of a composition comprising adding thereto an olfactorily effective amount of a compound of claim 1.

26. A method of modifying the olfactory properties of a composition comprising adding thereto an olfactorily effective amount of a compound of claim 21.

27. A product produced by the method of claim 25.

28. A product produced by the method of claim 26.

* * * * *

UNITED STATES PATENT AND TRADEMARK OFFICE
CERTIFICATE OF CORRECTION

PATENT NO. : 5,403,823
DATED      : April 4, 1995
INVENTOR(S) : Walter C. Frank

It is certified that error appears in the above-indentified patent and that said Letters Patent is hereby corrected as shown below:

Column 29, line 41, insert --,-- after "are" and insert --,-- after "independently".

Column 29, line 48, insert --,-- after "$R^3$" and insert --,-- after "independently".

Signed and Sealed this

Eighteenth Day of July, 1995

Attest:

BRUCE LEHMAN

Attesting Officer     Commissioner of Patents and Trademarks